US011499189B2

(12) United States Patent
Shen

(10) Patent No.: US 11,499,189 B2
(45) Date of Patent: Nov. 15, 2022

(54) MITIGATING ADVERSE IMPACTS OF DETECTION SYSTEMS ON NUCLEIC ACIDS AND OTHER BIOLOGICAL ANALYTES

(71) Applicant: OMNIOME, INC., San Diego, CA (US)

(72) Inventor: Min-Jui Richard Shen, San Diego, CA (US)

(73) Assignee: PACIFIC BIOSCIENCES OF CALIFORNIA, INC., Menlo Park, CA (US)

(*) Notice: Subject to any disclaimer, the term of this patent is extended or adjusted under 35 U.S.C. 154(b) by 463 days.

(21) Appl. No.: 16/783,488

(22) Filed: Feb. 6, 2020

(65) Prior Publication Data
US 2020/0263246 A1    Aug. 20, 2020

Related U.S. Application Data

(60) Provisional application No. 62/805,495, filed on Feb. 14, 2019.

(51) Int. Cl.
C12Q 1/6869 (2018.01)
C12Q 1/6876 (2018.01)
G01N 21/64 (2006.01)

(52) U.S. Cl.
CPC ........ *C12Q 1/6869* (2013.01); *C12Q 1/6876* (2013.01); *G01N 21/6428* (2013.01); *C12Q 2565/10* (2013.01); *C12Q 2565/40* (2013.01); *G01N 2021/6439* (2013.01)

(58) Field of Classification Search
CPC ............... C12Q 1/6869; C12Q 1/6876; C12Q 21/6428; C12Q 2565/10; C12Q 2565/40; C12Q 2525/186; C12Q 2527/137; C12Q 2535/122; C12Q 2563/107; G01N 21/6428; G01N 2021/6439
See application file for complete search history.

(56) References Cited

U.S. PATENT DOCUMENTS

| | | |
|---|---|---|
| 5,695,934 A | 12/1997 | Brenner |
| 5,863,722 A | 1/1999 | Brenner |
| 5,888,737 A | 3/1999 | DuBridge et al. |
| 6,140,489 A | 10/2000 | Brenner |
| 6,175,002 B1 | 1/2001 | DuBridge et al. |
| 6,266,459 B1 | 7/2001 | Walt et al. |
| 6,355,431 B1 | 3/2002 | Chee et al. |
| 6,770,441 B2 | 8/2004 | Dickinson et al. |
| 6,859,570 B2 | 2/2005 | Walt et al. |
| 7,041,812 B2 | 5/2006 | Kumar et al. |
| 7,057,026 B2 | 6/2006 | Barnes et al. |
| 7,211,414 B2 | 5/2007 | Hardin et al. |
| 7,315,019 B2 | 1/2008 | Turner et al. |
| 7,329,492 B2 | 2/2008 | Hardin et al. |
| 7,329,860 B2 | 2/2008 | Feng et al. |
| 7,405,281 B2 | 7/2008 | Xu et al. |
| 7,414,116 B2 | 8/2008 | Milton et al. |
| 7,427,673 B2 | 9/2008 | Balasubramanian et al. |
| 7,544,794 B1 | 6/2009 | Benner |
| 7,622,294 B2 | 11/2009 | Walt et al. |
| 7,956,171 B2 | 6/2011 | Siddiqi |
| 8,034,923 B1 | 10/2011 | Benner et al. |
| 8,071,755 B2 | 12/2011 | Efcavitch et al. |
| 8,236,532 B2 | 8/2012 | Ronaghi et al. |
| 8,298,792 B2 | 10/2012 | Ju et al. |
| 8,412,467 B2 | 4/2013 | Kain et al. |
| 8,753,816 B2 | 6/2014 | Rigatti et al. |
| 8,808,989 B1 | 8/2014 | Efcavitch et al. |
| 8,914,241 B2 | 12/2014 | Kain et al. |
| 8,951,781 B2 | 2/2015 | Reed et al. |
| 9,115,353 B2 | 8/2015 | Klausing et al. |
| 9,193,996 B2 | 11/2015 | Buermann et al. |
| 9,217,178 B2 | 12/2015 | Fedurco et al. |
| 9,399,798 B2 | 7/2016 | Stupi et al. |
| 10,077,470 B2 | 9/2018 | Vijayan et al. |

(Continued)

FOREIGN PATENT DOCUMENTS

| | | |
|---|---|---|
| WO | 91/006678 | 5/1991 |
| WO | 00/63437 | 1/2002 |

(Continued)

OTHER PUBLICATIONS

PCT/US2020/016956, International Search Report and Written Opinion, dated Jun. 2, 2020, 10 pages.
PCT/US2020/016956, "International Preliminary Report on Patentability", dated Aug. 26, 2021, 7 pages.
Bentley et al., "Accurate Whole Human Genome Sequencing Using Reversible Terminator Chemistry", Nature, vol. 456, No. 7218, Nov. 6, 2008, pp. 53-59.
EP20709092.9, "Office Action", dated May 23, 2022, 3 pages.

*Primary Examiner* — Narayan K Bhat
(74) *Attorney, Agent, or Firm* — Kilpatrick Townsend & Stockton LLP

(57) ABSTRACT

A method for sequencing a population of nucleic acids, which includes (a) binding the population of nucleic acids with a fractionally labeled mixture of nucleotides, thereby forming a fractionally labeled population of nucleic acids, wherein the mixture includes nucleotide cognates for a common base type in the templates, and wherein a fraction of the nucleotide cognates for the common base type in the mixture are exogenously labeled nucleotides that produce a signal that is not produced by other nucleotide cognates for the common base type in the mixture; (b) detecting the signal from the fractionally labeled population of nucleic acids; and (c) repeating (a) and (b) using a second mixture of the fractionally labeled nucleotides, wherein the fraction of the exogenously labeled nucleotides is higher in the second mixture.

20 Claims, No Drawings

(56) References Cited

U.S. PATENT DOCUMENTS

| | | |
|---|---|---|
| 10,161,003 B2 | 12/2018 | Stromberg et al. |
| 10,174,066 B2 | 1/2019 | Gordon et al. |
| 10,294,514 B2 | 5/2019 | Iyidogan et al. |
| 10,400,272 B1 | 9/2019 | Middleton et al. |
| 10,428,378 B2 | 10/2019 | Iyidogan et al. |
| 10,443,098 B2 | 10/2019 | Vijayan et al. |
| 2008/0108082 A1 | 5/2008 | Rank et al. |
| 2009/0247414 A1 | 10/2009 | Obradovic et al. |
| 2010/0111768 A1 | 5/2010 | Baneijee et al. |
| 2014/0080721 A1 | 3/2014 | Klausing et al. |
| 2017/0022553 A1* | 1/2017 | Vijayan ............... C12Q 1/6869 |
| 2017/0327801 A1 | 11/2017 | Kamtekar et al. |
| 2018/0073071 A1 | 3/2018 | Ju et al. |
| 2018/0187245 A1 | 7/2018 | Dambacher et al. |
| 2018/0208983 A1 | 7/2018 | Dambacher et al. |
| 2018/0274024 A1 | 9/2018 | Ju et al. |
| 2019/0010183 A1 | 1/2019 | Bjornson et al. |
| 2019/0048404 A1 | 2/2019 | Dambacher |
| 2019/0119740 A1 | 4/2019 | Ahn et al. |
| 2019/0241945 A1 | 8/2019 | Malyshev et al. |
| 2019/0338352 A1 | 11/2019 | Nemiroski et al. |
| 2020/0010885 A1 | 1/2020 | Malyshev et al. |
| 2020/0032317 A1 | 1/2020 | Rohrman et al. |
| 2020/0032322 A1 | 1/2020 | Subramanian et al. |
| 2022/0010370 A1* | 1/2022 | Zhao .................... C12Q 1/6869 |

FOREIGN PATENT DOCUMENTS

| | | |
|---|---|---|
| WO | 2004/018497 | 3/2004 |
| WO | 2007/123744 | 11/2007 |
| WO | 2010036311 A2 | 4/2010 |
| WO | 2013096692 A1 | 6/2013 |
| WO | 2017184996 A1 | 10/2017 |

* cited by examiner

MITIGATING ADVERSE IMPACTS OF DETECTION SYSTEMS ON NUCLEIC ACIDS AND OTHER BIOLOGICAL ANALYTES

CROSS-REFERENCE TO RELATED APPLICATION

This application is based on, and claims the benefit of, U.S. Provisional Application No. 62/805,495, filed Feb. 14, 2019, and which is incorporated herein by reference.

BACKGROUND

The present disclosure relates generally to detection of analytes and has specific applicability to sequencing of nucleic acids.

Detection of specific analytes in complex samples is a fundamental goal for biological assays that underly a wide variety of clinical and laboratory procedures. Such assays are typically designed to achieve specificity of detection while minimizing damaging effects of the detection conditions used on the samples and while preventing the detection conditions from creating artifacts and biases that would skew the accuracy of the assay results. Luminescence provides a salient example of a phenomenon that provides advantages of detection specificity but not without risks of adversely impacting the sample under analysis. Luminescent analytes, when exposed to light of an appropriate wavelength, will emit luminescence that can be detected using any of a variety of optical detection devices. Although the luminescence is typically specific for the analyte of interest due to low background luminescence of most samples, light is a form of electromagnetic irradiation that can cause damage to the samples.

The adverse impacts of electromagnetic radiation can be partially mitigated, for example, by minimizing the amount of time that the sample is exposed to the radiation or by minimizing the intensity of the radiation used. Unfortunately, this is not always possible. For example, nucleic acid sequencing presents unique challenges due to the extended amount of time that the sample spends being exposed to radiation, for example, over repeated detection cycles. A variety of nucleic acid sequencing methods employ luminescent components (e.g. fluorescently labeled nucleotides) as probes for the chemical structure of the nucleic acid. In many cases, a population of nucleic acids is evaluated via iterative cycles, each cycle including steps of delivering luminescent components to the nucleic acids, irradiating the nucleic acids with light in the presence of the luminescent components and detecting emitted luminescence to identify interactions between the luminescent components and the nucleic acids. The sequence of the nucleic acids is then determined based on observations of which luminescent components interact with the nucleic acids in each cycle. Radiation damage to nucleic acids is often manifested as reduced sequence read length or loss of sequence read accuracy.

Thus, there exists a need to improve stability for clinical and laboratory samples that are evaluated using techniques that have potential to degrade the samples, such as luminescence techniques.

BRIEF SUMMARY

The present disclosure provides a method for sequencing a population of nucleic acids, wherein the nucleic acids have templates sharing a common sequence. The method can include the steps of (a) binding the population of nucleic acids with a first fractionally labeled mixture of nucleotides, thereby forming a first fractionally labeled population of nucleic acids, wherein the first mixture includes nucleotide cognates for a common base type in the templates, and wherein a fraction of the nucleotide cognates for the common base type in the mixture are exogenously labeled nucleotides that produce a signal that is not produced by other nucleotide cognates for the common base type in the mixture; (b) detecting the signal from the fractionally labeled population of nucleic acids; and (c) repeating (a) and (b) using a second mixture of the fractionally labeled nucleotides, wherein the fraction of the exogenously labeled nucleotides is higher in the second mixture compared to the first mixture.

The present disclosure also provides a method for sequencing a population of nucleic acids, wherein the method includes subjecting a population of primer-template nucleic acid hybrids to multiple cycles of a nucleic acid sequencing process, wherein the templates share a common sequence, wherein each of the cycles includes (a) forming a mixed population including primer-template nucleic acid hybrids that are bound to a first nucleotide type and primer-template nucleic acid hybrids that are bound to a second nucleotide type, wherein the first nucleotide type has an exogenous label that produces a first signal and wherein the second nucleotide type is substantially devoid of labels that produce the first signal, wherein the first and second nucleotide types are cognates for the same base type in the template, and (b) detecting the signal from the mixed population, wherein the fraction of the first nucleotide type compared to the second nucleotide type is increased in the mixed population over at least two of the cycles of the nucleic acid sequencing process.

DETAILED DESCRIPTION

The present disclosure provides compositions, methods and apparatuses for mitigating damage to samples that are observed with the assistance of labeled reagents. Many assays that are used for such purposes are configured such that an ensemble of analytes is detected using a plurality of labeled reagents. For assays in which the analytes share at least one common characteristic that is under evaluation, and in which the labeled reagents are the same as each other, the results of the assay will provide an average characteristic for the ensemble. It is generally believed that the reagents should be uniformly labeled to achieve consistent results, for example, to avoid differential interactions that labeled and unlabeled species of the reagent may have with the analyte of interest. Labeling of all the reagents in the plurality is also favored under the rationale that increasing the amount of signal that will be detected from the ensemble, will in turn increases the sensitivity and limit of detection for the assay.

Moreover, in many assays, signal from the plurality of labeled reagents can decay over the course of detection. Typically, all of the reagents in the plurality are labeled under the rationale that starting the assay with a high signal to noise will prolong the observable lifetime of the ensemble before signal decay crosses below the threshold of detectability. In luminescent systems, signal decay can also be addressed by the addition of photoprotective reagents to the assay. For example, antioxidants such as ascorbate or gallic acid have been shown to protect nucleic acids during fluorescence-based sequencing by synthesis processes. See, for example, U.S. Pat. No. 9,115,353 or 9,217,178, each of which is incorporated herein by reference. Another approach that has been used with some success for protecting nucleic acids during fluorescence-based sequencing by synthesis processes is to reduce the intensity of radiation that contacts the sample or to reduce the amount of time the sample is exposed to the radiation. See, for example, U.S. Pat. No. 8,914,241, which is incorporated herein by reference. Such approaches can be beneficial, but do not fully prevent signal decay and detection artifacts.

Several nucleic acid sequencing procedures employ ensemble-based detection. In many procedures, nucleic acid fragments are amplified to form clusters or colonies on solid supports. An individual cluster or colony contains an ensemble of amplicons sharing a common sequence that is derived from a target nucleic acid template. Ensemble-based sequencing methods benefit from a synchronous, step-wise readout of the template sequence that is shared by the members of the cluster or colony. The ensemble is typically detected as a whole, such that individual nucleic acid molecules are not resolved, one from another, within the ensemble. This contrasts with sequencing techniques that employ single molecule-based detection. In the latter technique, degradation or damage to a single template nucleic acid can result in a missed base call, which in turn results in a gap in the sequence read; or in termination of the read altogether, which in turn produces a truncated read. Degradation and damage to the template nucleic acids can also occur in ensemble-based sequencing, but so long as undamaged templates remain in the ensemble, the sequence can still be read out. Sequencing can continue so long as there is a sufficient fraction of undamaged templates to provide a level of signal purity that is resolved over background noise.

Damage to templates in an ensemble-based sequencing technique can manifest as an apparent decay in signal purity (i.e. also observable as a decrease in signal to noise). Particular configurations of the methods, compositions and apparatus set forth herein can be used to gain apparent signal purity in later cycles of a sequencing run in trade for reducing the intensity of the signal produced in the earlier cycles of the run. In such configurations, the sequencing run can be performed using a fractionally labeled plurality of reagents, wherein the fraction of the reagents that are labeled increases as the run proceeds. For example, a plurality of reagents of one type can have a low fraction of labeled individuals, compared to unlabeled individuals of the same type, in early cycles of the run. Then, in later cycles, the fraction of labeled individuals of that reagent type can be increased. By way of more specific example, a sequencing technique that employs labeled nucleotides that are cognates for a particular base type in the template nucleic acid can be carried out such that early cycles employ a mixture of nucleotides in which only 25% of the nucleotide cognates for the particular base type have a label that produces a desired signal (i.e. 75% of the nucleotide cognates for that particular base type will substantially lack any label that produces the desired signal). As the run progresses the fraction of the nucleotide cognates for the particular base type that are labeled can be increased, for example, up to 100%.

Although not intending to be limited by mechanism, using reduced label fraction in early cycles of a sequencing run is believed to preserve the nucleic acids that are being sequenced by reducing the local concentration of harmful reactive species generated by electromagnetic radiation. When a population of luminescent labels is irradiated at an appropriate wavelength, the labels transition from ground state to an excited state. Luminescence is emitted when the labels return to the ground state. However, some of the labels that are in the excited state will produce free radicals rather than luminescence. These free radicals are highly reactive and can cause damage to molecules in their vicinity. By reducing the number of labels in a nucleic acid ensemble, the methods set forth herein effectively minimize the local concentration of damaging free radicals, thereby helping to preserve nucleic acids in the ensemble.

The methods, compositions and apparatus set forth herein for titrating the fraction of labeled species in an analytical assay can be used as an alternative or supplement to other techniques known in the art for reducing photodamage. For example, relatively low intensity of radiation and/or relatively short irradiation time can be used in early cycles of a sequencing run and then as the run proceeds the intensity and/or duration of irradiation can be increased. The types of changes in irradiation properties need not be employed when titrating label fraction as set forth herein. However, if desired, both techniques can be used in combination. For example, techniques set forth in U.S. Pat. No. 8,914,241 (which is incorporated herein by reference) can be modified to employ methods, compositions or apparatus set forth herein. Moreover, photoprotective reagents, such as reducing agents or photomasking agents that are set forth herein, or in references cited herein, can be used in combination with methods for titrating label fraction. Alternatively, the methods set forth herein need not employ photoprotective reagents.

Various aspects and embodiments of the present invention are set forth herein in the context of nucleic acid sequencing techniques. Those skilled in the art will recognize that other assay methods can also benefit. For example, any of a variety of assays that observe changes to a sample as labeled reagents are added can be modified to employ titration of fractionally labeled reagents. Such assays can include those carried out for spatial resolution of ensembles in a fluorescent microscope or those that utilize a fluorometer to detect ensembles in solution.

Terms used herein will be understood to take on their ordinary meaning in the relevant art unless specified otherwise. Several terms used herein and their meanings are set forth below.

As used herein, the term "amplicon" refers to the product of copying a nucleic acid. The product can have a nucleotide sequence that is the same as or complementary to at least a portion of the nucleic acid that was copied. An amplicon can be produced by any of a variety of amplification methods that use the nucleic acid, or an amplicon thereof, as a template including, for example, polymerase chain reaction (PCR), rolling circle amplification (RCA), multiple displacement amplification, bridge amplification or the like.

As used herein, the term "array" refers to a collection of molecules that is attached to one or more solid supports such that the molecules at one site can be distinguished from molecules at other sites. An array can include different molecules that are each located at different addressable sites on a solid support. Alternatively, an array can include separate solid supports each functioning as a site that bears a different molecule, wherein the different molecules can be identified according to the locations of the solid supports on a surface to which the solid supports are attached, or according to the locations of the solid supports in a liquid such as a fluid stream. The molecules of the array can be, for example, nucleotides, nucleic acid primers, nucleic acid templates or nucleic acid enzymes such as polymerases, ligases, exonucleases or combinations thereof.

As used herein, the term "binary complex" refers to an intermolecular association between a polymerase and a primed template nucleic acid, substantially lacking a monomeric nucleotide molecule such as a next correct nucleotide for the primed template nucleic acid.

As used herein, the term "blocking moiety," when used in reference to a nucleotide, means a part of the nucleotide that inhibits or prevents the 3' oxygen of the nucleotide from forming a covalent linkage to the next correct nucleotide during a nucleic acid polymerization reaction. The blocking moiety of a "reversibly terminated" nucleotide can be removed from the nucleotide, or otherwise modified, to allow the 3'-oxygen of the nucleotide to covalently link to a next correct nucleotide. Such a blocking moiety is referred to herein as a "reversible terminator moiety." Exemplary reversible terminator moieties are set forth in U.S. Pat. Nos. 7,427,673; 7,414,116; 7,057,026; 7,544,794 or 8,034,923; or PCT publications WO 91/06678 or WO 07/123744, each of which is incorporated herein by reference. A nucleotide that has a blocking moiety or reversible terminator moiety can be at the 3' end of a nucleic acid, such as a primer, or can be a monomer that is not covalently attached to a nucleic acid. A blocking moiety can be present at the 3' end of a nucleic acid that participates in formation of a ternary complex.

As used herein, the term "bound" can refer to an association or attachment between molecules that is non-covalent or covalent in nature. For example, a monomeric nucleotide can be non-covalently bound to nucleic acid via a stabilized ternary complex. Alternatively, a nucleotide can be covalently bound to a nucleic acid via polymerase catalyzed formation of a covalent bond between the 5' phosphate of the nucleotide and the 3' oxygen of the nucleic acid.

As used herein, the term "catalytic metal ion" refers to a metal ion that facilitates phosphodiester bond formation between the 3'-oxygen of a nucleic acid (e.g., a primer) and the phosphate of an incoming nucleotide by a polymerase. A "divalent catalytic metal cation" is a catalytic metal ion having a valence of two. Catalytic metal ions can be present at concentrations that stabilize formation of a complex between a polymerase, nucleotide, and primed template nucleic acid.

As used herein, the term "common," when used in reference to a characteristic of two or more members of a population, means the characteristic is the same for the two or more members. For example, a "common sequence" is a sequence of nucleotides that is the same for two or more nucleic acid molecules. A sequence that is common to two or more nucleic acids can include all or part of the nucleic acids that are being compared. The common sequence can have a length of at least 5, 10, 25, 50, 100, 500, 1000 or more nucleotides. Alternatively or additionally, the length can be at most 1000, 500, 100, 50, 25, 10, 5 or fewer nucleotides.

The term "comprising" is intended herein to be open-ended, including not only the recited elements, but further encompassing any additional elements.

As used herein, the term "cycle," when used in reference to a sequencing process, refer to the portion of a sequencing run that is repeated to indicate the presence of a nucleotide. Typically, a cycle includes several steps such as steps for delivery of reagents, washing away unreacted reagents and detection of signals indicative of changes occurring in response to added reagents.

As used herein, the term "deblock" means to remove or modify a reversible terminator moiety of a nucleotide to render the nucleotide extendable. For example, the nucleotide can be present at the 3' end of a primer such that deblocking renders the primer extendable. Exemplary deblocking reagents and methods are set forth in U.S. Pat. Nos. 7,427,673; 7,414,116; 7,057,026; 7,544,794 or 8,034,923; or PCT publications WO 91/06678 or WO 07/123744, each of which is incorporated herein by reference.

As used herein, the term "each," when used in reference to a collection of items, is intended to identify an individual item in the collection but does not necessarily refer to every item in the collection. Exceptions can occur if explicit disclosure or context clearly dictates otherwise.

As used herein, the term "exogenous," when used in reference to a moiety of a molecule, means a chemical moiety that is not present in a natural analog of the molecule. For example, an exogenous label of a nucleotide is a label that is not present on a naturally occurring nucleotide. Similarly, an exogenous label that is present on a polymerase is not found on the polymerase in its native milieu.

As used herein, the term "extendable," when used in reference to a nucleotide, means that the nucleotide has an oxygen or hydroxyl moiety at the 3' position, and is capable of forming a covalent linkage to a next correct nucleotide if and when incorporated into a nucleic acid. An extendable nucleotide can be at the 3' position of a primer or it can be a monomeric nucleotide. A nucleotide that is extendable will lack blocking moieties such as reversible terminator moieties.

As used herein, the term "extension," when used in reference to a nucleic acid, means a process of adding at least one nucleotide to the 3' end of the nucleic acid. The term "polymerase extension," when used in reference to a nucleic acid, refers to a polymerase catalyzed process of adding at least one nucleotide to the 3' end of the nucleic acid. A nucleotide or oligonucleotide that is added to a nucleic acid by extension is said to be incorporated into the nucleic acid. Accordingly, the term "incorporating" can be used to refer to the process of joining a nucleotide or oligonucleotide to the 3' end of a nucleic acid by formation of a phosphodiester bond.

As used herein, the term "fractionally labeled," when used in reference to a population of molecules, means that some of the molecules in the population are bound to a particular type of label but not all of the molecules in the population are bound to a label of that particular type. For example, some of the molecules in the population can be bound to a fluorophore that emits fluorescence at a particular wavelength and other molecules in the population are not bound to a fluorophore that emits at that particular wavelength. In some configurations, at most 99%, 90%, 80%, 70%, 60%, 50%, 40%, 30%, 20%, 10% or 1% of the molecules in a fractionally labeled population can be attached to a particular label. In some cases, any one of these exemplary upper limits can also be defined by a lower limit such that, for example, at least 1%, 10%, 20%, 30%, 40%, 50%, 60%, 70%, 80%, 90% or 99% of the molecules in the fractionally labeled population have the particular label.

As used herein, the term "immobilized," when used in reference to a molecule, refers to direct or indirect, covalent or non-covalent attachment of the molecule to a solid support. In some configurations, covalent attachment may be preferred, but generally all that is required is that the molecules (e.g. nucleic acids) remain attached to the support under the conditions in which it is intended to use the support.

As used herein, the term "label" refers to a molecule, or moiety thereof, that provides a detectable characteristic. The detectable characteristic can be, for example, an electrical property such as charge polarity (e.g. positive charge, negative charge or neutral charge for a label) or charge magnitude (e.g. number of elementary charges present in a label);

optical property such as absorbance of radiation, fluorescence emission, luminescence emission, fluorescence lifetime, fluorescence polarization, or the like; Rayleigh and/or Mie scattering; binding affinity for a ligand or receptor; magnetic properties; mass; radioactivity or the like. Exemplary labels include, without limitation, a luminophore (e.g. fluorophore), chromophore, nanoparticle (e.g., gold, silver, carbon nanotubes), heavy atom, radioactive isotope, mass label, magnetic label, charge label (e.g. positive charge label or negative charge label), spin label, receptor, ligand, or the like.

As used herein, the term "monoclonal," when used in reference to a population of nucleic acids, means that the nucleic acids in the population have substantially the same nucleotide sequence. The nucleotide sequence can include at least 25, 50, 100, 500 or 1000 nucleotides of a nucleic acid molecule. Typically, all nucleic acids in a monoclonal population will have the same nucleotide sequence. However, a monoclonal population can include nucleic acids that differ by a small number of single nucleotide differences, for example due to copying errors. For example, a member of a monoclonal population can differ from other members by no more than a single nucleotide difference per 1000 nucleotide sequence.

As used herein, the term "next correct nucleotide" refers to the nucleotide or nucleotide type that will bind and/or incorporate at the 3' end of a primer to complement a base in a template strand to which the primer is hybridized. The base in the template strand is referred to as the "next template base" and is immediately 5' of the base in the template that is hybridized to the 3' end of the primer. The next correct nucleotide can be referred to as the "cognate" of the next template base and vice versa. Cognate nucleotides that interact with each other in a ternary complex or in a double stranded nucleic acid are said to "pair" with each other. In accordance with Watson-Crick pairing rules adenine (A) pairs with thymine (T) or uracil (U), and cytosine (C) pairs with guanine (G). A nucleotide having a base that is not complementary to the next template base is referred to as an "incorrect", "mismatch" or "non-cognate" nucleotide for the next template base.

As used herein, the term "non-catalytic metal ion" refers to a metal ion that, when in the presence of a polymerase enzyme, does not facilitate phosphodiester bond formation needed for chemical incorporation of a nucleotide into a primer. A non-catalytic metal ion may interact with a polymerase, for example, via competitive binding compared to catalytic metal ions. Accordingly, a non-catalytic metal ion can act as an inhibitory metal ion that inhibits phosphodiester bond formation by the polymerase. A "divalent non-catalytic metal ion" is a non-catalytic metal ion having a valence of two. Examples of divalent non-catalytic metal ions include, but are not limited to, $Ca^{2+}$, $Zn^{2+}$, $Co^{2+}$, $Ni^{2+}$, and $Sr^{2+}$. The trivalent $Eu^{3+}$ and $Tb^{3+}$ ions are non-catalytic metal ions having a valence of three.

As used herein, the term "nucleotide" can be used to refer to a native nucleotide or analog thereof. Examples include, but are not limited to, nucleotide triphosphates (NTPs) such as ribonucleotide triphosphates (rNTPs), deoxyribonucleotide triphosphates (dNTPs), or non-natural analogs thereof such as dideoxyribonucleotide triphosphates (ddNTPs) or reversibly terminated nucleotide triphosphates (rtNTPs).

As used herein, the term "polymerase" can be used to refer to a nucleic acid synthesizing enzyme, including but not limited to, DNA polymerase, RNA polymerase, reverse transcriptase, primase and transferase. Typically, the polymerase has one or more active sites at which nucleotide binding and/or catalysis of nucleotide polymerization may occur. The polymerase may catalyze the polymerization of nucleotides to the 3' end of the first strand of the double stranded nucleic acid molecule. For example, a polymerase catalyzes the addition of a next correct nucleotide to the 3' oxygen group of the first strand of the double stranded nucleic acid molecule via a phosphodiester bond, thereby covalently incorporating the nucleotide to the first strand of the double stranded nucleic acid molecule. Optionally, a polymerase need not be capable of nucleotide incorporation under one or more conditions used in a method set forth herein. For example, a mutant polymerase may be capable of forming a ternary complex but incapable of catalyzing nucleotide incorporation.

As used herein, the terms "primer-template," "primer-template nucleic acid" or "primer-template nucleic acid hybrid" refer to a nucleic acid having a double stranded region such that one of the strands is a primer and the other strand is a template. The two strands can be parts of a contiguous nucleic acid molecule (e.g. a hairpin structure) or the two strands can be separable molecules that are not covalently attached to each other.

As used herein, the term "primer" refers to a nucleic acid having a sequence that binds to a nucleic acid at or near a template sequence. Generally, the primer binds in a configuration that allows replication of the template, for example, via polymerase extension of the primer. The primer can be a first portion of a nucleic acid molecule that binds to a second portion of the nucleic acid molecule, the first portion being a primer sequence and the second portion being a primer binding sequence (e.g. a hairpin primer). Alternatively, the primer can be a first nucleic acid molecule that binds to a second nucleic acid molecule having the template sequence. A primer can consist of DNA, RNA or analogs thereof. A primer can have an extendible 3' end or a 3' end that is blocked from primer extension.

As used herein, the term "signal" refers to energy or coded information that can be selectively observed over other energy or information such as background energy or background information. A signal can have a desired or predefined characteristic. For example, an electrical signal can be characterized or observed by one or more of intensity, polarity, current, voltage, impedance, resistance, conductance, capacity, electric field strength or the like. An optical signal can be characterized by one or more of intensity, wavelength, absorption, luminescence excitation, luminescence emission, luminescence lifetime, anisotropy, polarity or the like. Absence of signal is understood to be a signal level of zero or a signal level that is not meaningfully distinguished from noise.

As used herein, the term "site," when used in reference to an array, means a location in an array where a particular molecule is present. A site can contain only a single molecule or it can contain a population of several molecules of the same species (i.e. an ensemble of the molecules). Alternatively, a site can include a population of molecules that includes different species (e.g. a population of ternary complexes having different template sequences). Sites of an array are typically discrete. The discrete sites can be contiguous or they can have interstitial spaces between each other. An array useful herein can have, for example, sites that are separated by less than 100 microns, 50 microns, 10 microns, 5 microns, 1 micron, or 0.5 micron. Alternatively or additionally, an array can have sites that are separated by greater than 0.5 micron, 1 micron, 5 microns, 10 microns, 50 microns or 100 microns. The sites can each have an area of less than 1 square millimeter, 500 square microns, 100 square microns, 25 square microns, 1 square micron or less. A site of an array may also be referred to herein as a 'feature' of the array.

As used herein, the term "solid support" refers to a rigid substrate that is insoluble in aqueous liquid. The substrate can be non-porous or porous. The substrate can optionally be capable of taking up a liquid (e.g. due to porosity) but will typically be sufficiently rigid that the substrate does not swell substantially when taking up the liquid and does not contract substantially when the liquid is removed by drying. A nonporous solid support is generally impermeable to liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers.

As used herein, the term "substantially devoid" means being without an effective or detectable amount of a particular thing or characteristic. Whether or not a detectable amount is present can be understood to be relative to a particular detection method or apparatus. Taking a nucleic acid sequencing process as an example, a population of nucleotide cognates for a particular base type can be used in the process and the population can be said to be substantially devoid of a label if the label is not detected in the sequencing process. Continuing with this example, the population can be said to be substantially devoid of the label if the amount of signal detected from the label is not significant compared to background noise output by the detector.

As used herein, the term "ternary complex" refers to an intermolecular association between a polymerase, a double stranded nucleic acid and a nucleotide. Typically, the polymerase facilitates interaction between a next correct nucleotide and a template strand of the primed nucleic acid. The next correct nucleotide can interact with the template strand via Watson-Crick hydrogen bonding. The term "stabilized ternary complex" means a ternary complex having promoted or prolonged existence or a ternary complex for which disruption has been inhibited. Stabilization of the ternary complex prevents covalent incorporation of the nucleotide component of the ternary complex into the primed nucleic acid component of the ternary complex.

As used herein, the term "type" is used to identify molecules that share the same chemical structure. For example, a mixture of nucleotides can include several dCTP molecules. The dCTP molecules will be understood to be the same type of nucleotide as each other, but a different type of nucleotide compared to dATP, dGTP, dTTP etc. Similarly, individual DNA molecules that have the same sequence of nucleotides are the same type, whereas DNA molecules with different sequences are different types. The term "type" can also identify moieties that share the same chemical structure. For example, the cytosine bases in a template nucleic acid will be understood to be the same type of base as each other independent of their position in the template sequence.

The embodiments set forth below and recited in the claims can be understood in view of the above definitions.

The present disclosure provides a method for sequencing a population of nucleic acids, wherein the nucleic acids have templates sharing a common sequence. The method can include steps of (a) binding the population of nucleic acids with a first fractionally labeled mixture of nucleotides, thereby forming a fractionally labeled population of nucleic acids, wherein the first mixture includes nucleotide cognates for a common base type in the templates, and wherein a fraction of the nucleotide cognates for the common base type in the mixture are exogenously labeled nucleotides that produce a signal that is not produced by other nucleotide cognates for the common base type in the mixture; (b) detecting the signal from the fractionally labeled population of nucleic acids; and (c) repeating (a) and (b) using a second mixture of the fractionally labeled nucleotides, wherein the fraction of the exogenously labeled nucleotides is higher in the second mixture compared to the first mixture.

The present disclosure also provides a method for sequencing a population of nucleic acids that includes subjecting a population of primer-template nucleic acid hybrids to multiple cycles of a nucleic acid sequencing process, wherein the templates share a common sequence, wherein each of the cycles includes steps of: (a) forming a mixed population including primer-template nucleic acid hybrids that are bound to a first nucleotide type and primer-template nucleic acid hybrids that are bound to a second nucleotide type, wherein the first nucleotide type has an exogenous label that produces a first signal and wherein the second nucleotide type is substantially devoid of labels that produce the first signal, wherein the first and second nucleotide types are cognates for the same base type in the template, and (b) detecting the signal from the mixed population, wherein the fraction of the first nucleotide type compared to the second nucleotide type is increased in the mixed population over at least two of the cycles of the nucleic acid sequencing process.

A method of the present disclosure can employ a fractionally labeled mixture of nucleotides. The mixture can include at least two nucleotides that are cognates for the same base in a template nucleic acid, wherein one of the nucleotides contains a label moiety that produces a signal that is not produced by the other nucleotide in the mixture. The nucleotide that does not produce the signal that is detected can be referred to as a 'dark' nucleotide. However, use of the term dark nucleotide is not meant to imply the signal is necessarily a light signal only that the dark nucleotide is a nucleotide that is not detected in the fractionally labeled mixture. Typically, the labeled and dark nucleotides will have the same base moiety. For example, the labeled and dark nucleotides can have an adenine base moiety, the labeled and dark nucleotides can have a guanine base moiety, the labeled and dark nucleotides can have a cytosine base moiety, the labeled and dark nucleotides can have a thymine base moiety, or the labeled and dark nucleotides can have a uracil base moiety. However, in some cases the base moieties of the labeled and dark nucleotides can have different structures so long as the structural differences do not result in a substantial difference in the ability of the two base moieties to selectively pair with the same cognate base in a nucleic acid template under conditions employed in a method set forth herein. For example, one of the nucleotides in the mixture can have a thymine base moiety and the other nucleotide can have a uracil base moiety, whereby both nucleotides will selectively pair with an adenine base moiety in a template nucleic acid.

In particular configurations of the methods or compositions set forth herein, the labeled and dark nucleotides that are present in a fractionally labeled mixture of nucleotides will have base moieties that are cognates that selectively pair with an adenine base moiety in a template nucleic acid. Alternatively or additionally, labeled and dark nucleotides that are present in a fractionally labeled mixture of nucleotides will have base moieties that are cognates that selectively pair with a guanine base moiety in a template nucleic acid. Alternatively or additionally, labeled and dark nucleotides that are present in a fractionally labeled mixture of nucleotides will have base moieties that are cognates that selectively pair with a cytosine base moiety in a template nucleic acid. Alternatively or additionally, labeled and dark nucleotides that are present in a fractionally labeled mixture of nucleotides will have base moieties that are cognates that selectively pair with a thymine base moiety in a template nucleic acid.

Accordingly, a fractionally labeled mixture of nucleotides can include multiple subsets of nucleotides, wherein each subset includes labeled and dark nucleotides that are cognates for the same base type in a template nucleic acid. At least 1, 2, 3 or 4 of the subsets can be present in a fractionally labeled mixture of nucleotides, the subsets differing with respect to the base type in a template nucleic acid for which the nucleotides in the subset are cognates. Alternatively or additionally, a fractionally labeled mixture of nucleotides can contain no more than 4, 3, 2 or 1 of the subsets, the subsets differing with respect to the base type in a template nucleic acid for which the nucleotides in the subset are cognates. An exemplary subset of nucleotides can include cognates for an adenine base that are labeled to produce a particular signal and cognates for the adenine base that do not produce that particular signal. Alternatively or additionally, a subset of nucleotides can include cognates for a thymine base that are labeled to produce a particular signal and cognates for the thymine base that do not produce that particular signal. Alternatively or additionally, a subset of nucleotides can include cognates for a cytosine base that are labeled to produce a particular signal and cognates for the cytosine base that do not produce that particular signal. Alternatively or additionally, a subset of nucleotides can include cognates for a guanine base that are labeled to produce a particular signal and cognates for the guanine base that do not produce that particular signal.

For a typical fractionally labeled mixture of nucleotides that are cognates for a common base type, one of the nucleotides in the mixture will have a label moiety that is not present in the other nucleotide in the mixture. When used in an assay such as a nucleic acid sequencing procedure, one of the nucleotides in the fractionally labeled mixture will be substantially devoid of any labels that produce the signal that is detected from the label on the other nucleotide. However, in some cases the label moiety can be present in both nucleotides, but the label moiety in one of the nucleotides will be non-functional (e.g. due to binding of a signal quenching moiety).

As set forth above, a fractionally labeled mixture of nucleotides can include multiple subsets of nucleotides, wherein each subset includes at least one labeled nucleotide and at least one dark nucleotide, wherein the nucleotides in the subset are cognates for the same base type in a template nucleic acid. The labeled nucleotides in different subsets can be distinguished from each other based on different signals produced from the respective labels. For example, labeled nucleotides in a first subset, which are cognates for a first base type, can produce a first signal and labeled nucleotides in a second subset, which are cognates for a second base type, can produce a second signal, wherein the first signal is distinguished from the second signal in a method set forth herein. In addition to these two subsets of nucleotides, a fractionally labeled mixture of nucleotides can optionally include labeled nucleotides in a third subset, which are cognates for a third base type that can produce a third signal, wherein the third signal is distinguished from the first and second signals in a method set forth herein. As a further option, the fractionally labeled mixture of nucleotides can optionally include labeled nucleotides in a fourth subset, which are cognates for a fourth base type that can produce a fourth signal, wherein the fourth signal is distinguished from the first, second and third signals in a method set forth herein. As such, a fractionally labeled mixture of nucleotides can include at least 1, 2, 3 or 4 labels that each produce a unique signal, each label being associated with a cognate for a different base type in a template nucleic acid. Alternatively or additionally, a fractionally labeled mixture of nucleotides can include at most 4, 3, 2 or 1 labels that each produce a unique signal, each label being associated with a cognate for a different base type in a template nucleic acid.

In a fractionally labeled mixture of nucleotides, the fraction of nucleotide cognates for a particular base type that also have a label moiety that produces a particular signal, as compared to nucleotide cognates for the particular base type that do not produce the particular signal can be, for example, at least 0.1, 0.2, 0.3, 0.4, 0.5, 0.6, 0.7, 0.8, 0.9 or more. Alternatively or additionally, the fraction can be at most 0.9, 0.8, 0.7, 0.6, 0.5, 0.4, 0.3, 0.2 or 0.1.

In a method of the present disclosure, the fraction of nucleotide cognates for a particular base type that also have a label moiety that produces a particular signal, as compared to nucleotide cognates for the particular base type that do not produce the particular signal (i.e. a dark nucleotide) can be increased over the course of the method. The increase can be measured as a step function comparing the fraction for an earlier cycle to the fraction for a later cycle. Taking a cyclic sequencing run as an example, the fraction can increase by a step size of at least 1%, 5%, 10%, 25%, 50%, 75%, 90%, 2 fold, 5 fold, 10 fold, 50 fold or more from an earlier cycle to a later cycle of the run. Alternatively or additionally, the increase in the fraction from an earlier cycle to a later cycle can increase by a step size of no more than 50 fold, 10 fold, 5 fold, 2 fold, 90%, 75%, 50%, 25%, 10%, 5%, 1% or less. The cycles that are being compared can be contiguous with each other or non-contiguous with each other.

The increase in the fraction of nucleotide cognates for a particular base type that also have a label moiety that produces a particular signal, as compared to nucleotide cognates for the particular base type that do not produce the particular signal (i.e. dark nucleotide) can be measured overall for a cyclic sequencing run. Taking a cyclic sequencing run as an example, the fraction can cumulatively increase by at least 10%, 25%, 50%, 75%, 90%, 2 fold, 5 fold, 10 fold, 50 fold or more over the course of the run. Alternatively or additionally, the fraction can cumulatively increase over the course of the run by no more than 50 fold, 10 fold, 5 fold, 2 fold, 90%, 75%, 50%, 25%, 10% or less. The cumulative increase can occur over any number of steps including, for example, over at least 2, 3, 4, 5, 10, 25, 50, 100 or more steps up to and including the number of steps in the sequencing run. Alternatively or additionally, the cumulative increase can occur over no more than 1000, 500, 100, 50, 25, 10, 5, 4, 3, or 2 steps.

In some configurations the dark nucleotides in a fractionally labelled mixture of nucleotides will be reversibly terminated. This can be the case whether or not the labeled nucleotides in the subset are also reversibly terminated. The presence of a reversible terminator moiety on the non-signal generating nucleotide provides advantages for embodiments of the methods that employ Sequencing By Binding™ (SBB™) techniques. For example, the presence of reversible terminator moieties can mitigate the risk of phasing problems that would occur if extendable nucleotides were incorporated into a primer during an examination step or that would occur after the extendable nucleotides were carried over to a subsequent extension step. Phasing problems occur when some or all of the primers in an ensemble are extended by more than one nucleotide when only one nucleotide is intended to be added by extension. This in turn causes reduced signal from loss of in-phase primers, increased background signals due to out of phase primers, increased errors in the sequence read and decreased read length. Another advantage of using reversibly terminated versions of dark nucleotides in a fractionally labeled population of nucleotides is economy of reagent consumption and simplification of fluidic systems used for storing and delivering reagents. Specifically, for many SBB™ systems, the same pool of non-labeled, reversibly terminated nucleotides can be used both for the examination step and the extension step. Otherwise, the use of separate nucleotide species for those two steps would require additional reservoirs and fluidic manipulations.

Various aspects of fractional labeling are exemplified herein with regard to fractionally labeled mixtures of nucleotides. It will be understood that other reagents or assay components can be fractionally labeled. Taking sequencing procedures as an example, procedures that employ labeled polymerases can be modified to incorporate fractionally labeled mixtures of polymerases. Exemplary procedures that can be modified in this way include, but are not limited to, Sequencing By Binding™ (SBB™) procedures such as those set forth in U.S. Pat. Nos. 10,077,470 or 10,161,003, or US Pat. App. Pub. Nos. 2017/0314064 A1, 2018/0044727 A1, or 2018/0187245 A1, each of which is incorporated herein by reference. Other components for sequencing procedures that can be fractionally labeled include, but are not limited to, nucleic acid primers, nucleic acid templates, oligonucleotides used for ligation, exonucleases, nanopores or the like. Moreover, the aspects of fractional labeling that are exemplified herein for sequencing methods can be applied to other assays as will be apparent to those skilled in the art in view of the examples set forth herein.

Any of a variety of labels can be used in a method, composition or apparatus herein. Particularly useful labels are those that are optically detectable such as luminophores, fluorophores, chromophores, Raman scattering labels, plasmonic nanoparticles, luminescence quenchers or the like. Exemplary luminophores include, but are not limited to, fluorescent nanocrystals; quantum dots; green fluorescent protein and color shifted mutants thereof, phycobiliproteins such as phycocyanin and phycoerythrin, d-Rhodamine acceptor dyes including dichloro[R110], dichloro[R6G], dichloro[TAMRA], dichloro[ROX] or the like; fluorescein donor dye including fluorescein, 6-FAM, or the like; Cyanine dyes such as Cy3B; Alexa dyes, SETA dyes, Atto dyes such as atto 647N which forms a FRET pair with Cy3B and the like. Fluorophores include, but are not limited to, MDCC (7-diethylamino-3-[([(2-maleimidyl)ethyl]amino)carbonyl] coumarin), TET, HEX, Cy3, TMR, ROX, Texas Red, Cy5, LC red 705 and LC red 640. Exemplary quenchers include, but are not limited to, ZEN, IBFQ, BHQ-1, BHQ-2, DDQ-I, DDQ-11, Dabcyl, Qxl quencher, Iowa Black RQ, and IRDye QC-1. Other optically detectable labels known in the art such as those described in *Principles of Fluorescence Spectroscopy*, Joseph R. Lakowicz (Editor), Plenum Pub Corp, 2nd edition (July 1999) and the 6th Edition of *Molecular Probes Handbook* by Richard P. Hoagland (each of which is incorporated herein by reference, can be useful.

In some configurations of the methods, compositions or apparatus herein, a non-optical label can be used. Exemplary labels include, but are not limited to, radioactive labels, charge labels, pH labels, electromagnetic spin labels, and secondary labels. A secondary label is a binding moiety that can bind specifically to a partner moiety. For example, a ligand moiety can be attached to an assay component (e.g. a nucleotide used in a sequencing procedure), thereby allowing detection via specific affinity for labeled receptor. Exemplary pairs of binding moieties that can be used include, without limitation, antigen and immunoglobulin or active fragments thereof, such as FAbs; immunoglobulin and immunoglobulin (or active fragments, respectively); avidin and biotin, or analogs thereof having specificity for avidin; streptavidin and biotin, or analogs thereof having specificity for streptavidin; or carbohydrates and lectins. In some embodiments, the secondary label can be a chemically modifiable moiety. In this embodiment, labels having reactive functional groups can be incorporated into a reagent that is used in a sequencing procedure or other assay. Subsequently, the functional group can be covalently reacted with a primary label moiety. Suitable functional groups include, but are not limited to, amino groups, carboxy groups, maleimide groups, oxo groups, thiol groups or groups used for click chemistry reactions. Useful click chemistry reagents and methods are set forth in U.S. Pat. Nos. 6,737, 236; 7,375,234; 7,427,678 and 7,763,736, each incorporated herein by reference in its entirety For embodiments that use a secondary label, fractional labeling of a particular assay component can be achieved by titrating the fraction of either binding partner. Taking as an example a sequencing method that uses a fractionally labeled mixture of nucleotides, a first subset of the nucleotides can be linked to a ligand whereas a second subset of the nucleotides is substantially devoid of the ligand. The mixture can be contacted with a saturating amount of labeled receptors such that the first subset can generate a characteristic signal from the label that is bound via the receptor and the second subset, which does not bind the labeled receptor, does not produce the signal. In an alternative configuration for a sequencing method that uses a fractionally labeled mixture of nucleotides, all of the nucleotides in the mixture can be attached to a ligand and the mixture can be contacted with a subsaturating amount of labeled receptor such that only a fraction of the nucleotides bind to the labels that produce the characteristic signal. In yet another example, all of the nucleotides in the mixture can be attached to a ligand and the mixture can be contacted with a saturating amount of receptor; however, only a fraction of the receptor is labeled such that only a fraction of the nucleotides acquire labels that produce a characteristic signal and other nucleotides do not produce the characteristic signals since they acquire non-labeled receptors.

Any of a variety of chemistries known for attaching a label to a nucleotide can be used herein. For example, a label can be attached via linkage to the base moiety (e.g. purine or pyrimidine moiety) of a nucleotide. Exemplary linkages and labels that can be used to modify a base moiety are set forth, for example, in Bentley et al., *Nature* 456:53-59 (2008), WO 04/018497; WO 91/06678; WO 07/123744; U.S. Pat. Nos. 7,057,026; 7,329,492; 7,211,414; 7,315,019 or 7,405,281, and US Pat. App. Pub. No. 2008/0108082 A1, each of which is incorporated herein by reference. In some configurations, a label moiety is attached to a moiety other than the base moiety. For example, a label moiety can be attached to a phosphate moiety at the 5' position of the ribose moiety of a nucleotide. Exemplary linkages and labels that can be used to modify the 5' position are set forth in US Pat. App. Pub. Nos. 2017/0327801 or 2018/0073071 A1 or U.S. Pat. No. 7,041,812 or 7,405,281, each of which is incorporated herein by reference. In some configurations, a label moiety is attached to a ribose moiety other than the 5' position. For example, a label moiety can be linked to the 2' or 3' position of the ribose moiety.

A linker that is present in a nucleotide or other assay component set forth herein can be, but need not be, cleavable. Exemplary cleavable linkers are set forth in the previously cited references or in US Pat. App. Pub. No. 2018/0274024 A1, which is incorporated herein by reference. In alternative configurations, the linker can be stable to conditions used such that the covalent structure of the linker is not changed during any particular step, or throughout all steps, of a method set forth herein.

Optionally, a nucleotide (whether a native nucleotide or analog thereof) can have a nitrogenous base, five-carbon sugar, and phosphate group, wherein any moiety of the nucleotide may be modified, removed and/or replaced as compared to a native nucleotide. Nucleotides may be non-incorporable nucleotides (i.e. nucleotides that are incapable of reacting with the 3' oxygen of a primer to form a covalent linkage). Such nucleotides that are incapable of incorporation include, for example, monophosphate and diphosphate nucleotides. In another example, the nucleotide may contain modification(s) to the triphosphate group that render the nucleotide non-incorporable. Examples of non-incorporable nucleotides may be found in U.S. Pat. No. 7,482,120, which is incorporated by reference herein. In some embodiments, non-incorporable nucleotides may be subsequently modified to become incorporable. Non-incorporable nucleotides include, but are not limited to, alpha-phosphate modified nucleotides, alpha-beta nucleotide analogs, beta-phosphate modified nucleotides, beta-gamma nucleotide analogs, gamma-phosphate modified nucleotides, or caged nucleotides. Further examples of useful nucleotides are described in U.S. Pat. No. 8,071,755, which is incorporated by reference herein.

Nucleotides that are used in a method or system herein can include terminators that reversibly prevent subsequent nucleotide incorporation at the 3'-end of the primer after the nucleotide has been incorporated into the primer. For example, U.S. Pat. Nos. 7,544,794 and 8,034,923 (the disclosures of these patents are incorporated herein by reference) describe reversible terminators in which the 3'—OH group is replaced by a 3'-ONH2 moiety. Another type of reversible terminator is linked to the nitrogenous base of a nucleotide as set forth, for example, in U.S. Pat. No. 8,808,989 (the disclosure of which is incorporated herein by reference). Other reversible terminators that similarly can be used in connection with the methods described herein include those described in references cited elsewhere herein or in U.S. Pat. Nos. 7,956,171, 8,071,755, and 9,399,798 (the disclosures of these U.S. patents are incorporated herein by reference). In certain embodiments, a reversible terminator moiety can be removed from a primer, in a process known as "deblocking," allowing for subsequent nucleotide incorporation. Compositions and methods for deblocking are set forth in references cited herein in the context of reversible terminators.

Alternatively, nucleotides irreversibly prevent nucleotide incorporation at the 3'-end of the primer to which they have been incorporated. Irreversible nucleotides include 2', 3'-dideoxynucleotides (ddNTPs such as ddGTP, ddATP, ddTTP, ddCTP). Dideoxynucleotides lack the 3'—OH group of dNTPs that would otherwise participate in polymerase-mediated primer extension. Thus, the 3' position has a hydrogen moiety instead of the native hydroxyl moiety.

In particular embodiments, nucleotides that are used herein, for example, to participate in stabilized ternary complexes, do not include blocking groups (e.g. reversible terminators) that prevent subsequent nucleotide incorporation at the 3'-end of the primer after the nucleotide has been incorporated into the primer. This can be the case whether or not an extension step is carried out using nucleotide(s) having a blocking group (e.g. reversible terminator). Alternatively, nucleotides that participate in stabilized ternary complexes can include blocking groups (e.g. reversible terminators). For example, a fractionally labeled mixture of nucleotides can include labeled nucleotides that produce a particular signal and nucleotides that do not produce the particular signal, wherein both types of nucleotides are cognates for the same base type in a template nucleic acid, and wherein one or both types of the nucleotides have blocking groups.

In some embodiments, a nucleotide that is used herein, for example, to participate in forming a stabilized ternary complex, can include an exogenous label. An exogenously labeled nucleotide can include a reversible or irreversible terminator moiety, an exogenously labeled nucleotide can be non-incorporable, an exogenously labeled nucleotide can lack terminator moieties, an exogenously labeled nucleotide can be incorporable or an exogenously labeled nucleotide can be both incorporable and non-terminated.

Alternatively, a nucleotide that is used herein, for example, to participate in forming a ternary complex can lack exogenous labels (i.e. the nucleotide can be "non-labeled"). A non-labeled nucleotide can include a reversible or irreversible terminator moiety, a non-labeled nucleotide can be non-incorporable, a non-labeled nucleotide can lack terminator moieties, a non-labeled nucleotide can be incorporable, or a non-labeled nucleotide can be both incorporable and non-terminated. Non-labeled nucleotides can be present in a fractionally labeled mixture of nucleotides. It will be understood that one or more of the functions or moieties set forth herein for a nucleotide, or analog thereof, or otherwise known in the art for a nucleotide, or analog thereof, can be specifically omitted in a method or composition set forth herein.

Nucleic acids that are used in a method or composition herein can be DNA such as genomic DNA, synthetic DNA, amplified DNA, copy DNA (cDNA) or the like. RNA can also be used such as mRNA, ribosomal RNA, tRNA or the like. In some configurations RNA is reverse transcribed to produce DNA of the same or complementary sequence. Nucleic acid analogs can also be used as templates herein. Thus, template nucleic acids used herein can be derived from a biological source, synthetic source or amplification product. Primers used herein can be DNA, RNA or analogs thereof.

Particularly useful nucleic acid templates are genome fragments that include sequences identical to a portion of a genome. A population of genome fragments can include at least 5%, 10%, 20%, 30%, 40%, 50%, 60%, 70%, 75%, 80%, 85%, 90%, 95% or 99% of a genome. A genome fragment can have, for example, a sequence that is substantially identical to at least about 25, 50, 70, 100, 200, 300, 400, 500, 600, 700, 800, 900 or 1000 or more contiguous nucleotides of a genome. Alternatively or additionally, a genome fragment can have a sequence that is substantially identical to no more than $1 \times 10^5$, $1 \times 10^4$, $1 \times 10^3$, 800, 600, 400, 200, 100, 75, 50 or 25 contiguous nucleotides of a genome. A genome fragment can be DNA, RNA, or an analog thereof.

Exemplary organisms from which nucleic acids can be derived include, for example, a mammal such as a rodent, mouse, rat, rabbit, guinea pig, ungulate, horse, sheep, pig, goat, cow, cat, dog, primate, human or non-human primate; a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a *Dictyostelium discoideum*; a fungi such as *Pneumocystis carinii, Takifugu rubripes*, yeast, *Saccharamoyces cerevisiae* or *Schizosaccharomyces pombe*; or a *Plasmodium falciparum*. Nucleic acids can also be derived from a prokaryote such as a bacterium, *Escherichia coli*, staphylococci or *Mycoplasma pneumoniae*; an archae; a virus such as Hepatitis C virus or human immunodeficiency virus; or a viroid. Nucleic acids can be derived from a homogeneous culture or population of the above organisms or alternatively from a collection of several different organisms, for example, in a community or ecosystem. Nucleic acids can be isolated using methods known in the art including, for example, those described in Sambrook et al., *Molecular Cloning: A Laboratory Manual*, 3rd edition, Cold Spring Harbor Laboratory, New York (2001) or in Ausubel et al., *Current Protocols in Molecular Biology*, John Wiley and Sons, Baltimore, Md. (1998), each of which is incorporated herein by reference.

A template nucleic acid can be obtained from a preparative method such as genome isolation, genome fragmentation, gene cloning and/or amplification. The template can be obtained from an amplification technique such as polymerase chain reaction (PCR), rolling circle amplification (RCA), multiple displacement amplification (MDA) or the like. Exemplary methods for isolating, amplifying and fragmenting nucleic acids to produce templates for analysis on an array are set forth in U.S. Pat. No. 6,355,431 or 9,045,796, each of which is incorporated herein by reference. Amplification can also be carried out using a method set forth in Sambrook et al., *Molecular Cloning: A Laboratory Manual*, 3rd edition, Cold Spring Harbor Laboratory, New York (2001) or in Ausubel et al., *Current Protocols in Molecular Biology*, John Wiley and Sons, Baltimore, Md. (1998), each of which is incorporated herein by reference.

A nucleic acid or other component of a sequencing procedure (or other assay), can be attached to a solid support. The solid support can be made from any of a variety of materials used for analytical biochemistry. Suitable materials may include glass, polymeric materials, silicon, quartz (fused silica), borofloat glass, silica, silica-based materials, carbon, metals, an optical fiber or bundle of optical fibers, sapphire, or plastic materials. The particular material can be selected based on properties desired for a particular use. For example, materials that are transparent to a desired wavelength of radiation are useful for analytical techniques that will utilize radiation of that wavelength. Conversely, it may be desirable to select a material that does not pass radiation of a certain wavelength (e.g. being opaque, absorptive or reflective). Other properties of a material that can be exploited are inertness or reactivity to certain reagents used in a desired assay, such as sequencing nucleic acids or other assays set forth herein, or ease of manipulation, or low cost of manufacture.

A particularly useful solid support is a particle such as a bead or microsphere. Populations of beads can be used for attachment of nucleic acids or other components of a sequencing procedure (or other assay). In some embodiments, it may be useful to use a configuration whereby each bead has a single type of assay component. For example, an individual bead can be attached to a single type of template nucleic acid, a single type of ternary complex, a single type of nucleic acid primer, or a single type of nucleotide. Each bead can be attached to no more than a single molecule or, alternatively, each bead can be attached to an ensemble of molecules of a single type.

Different types of components need not be separated on a bead-by-bead basis. As such, a single bead can bear multiple different types of ternary complexes, template nucleic acids, primers, primer-template nucleic acid hybrids and/or nucleotides.

The composition of a bead can vary, depending for example, on the format, chemistry and/or method of attachment to be used. Exemplary bead compositions include solid supports, and chemical functionalities imparted thereto, used in protein and nucleic acid capture methods. Such compositions include, for example, plastics, ceramics, glass, polystyrene, melamine, methylstyrene, acrylic polymers, paramagnetic materials, thoria sol, carbon graphite, titanium dioxide, latex or cross-linked dextrans such as Sepharose™, cellulose, nylon, cross-linked micelles and Teflon™, as well as other materials set forth in "Microsphere Detection Guide" from Bangs Laboratories, Fishers Ind., which is incorporated herein by reference.

The geometry of a particle, bead or microsphere can correspond to a wide variety of different forms and shapes. For example, they can be symmetrically shaped (e.g. spherical or cylindrical) or irregularly shaped (e.g. controlled pore glass). In some configurations, beads can be porous, thus increasing the surface area available for capture of ternary complexes or other assay components. Exemplary sizes for beads used herein can range from nanometers to millimeters or from about 10 nm-1 mm.

In particular embodiments, beads can be arrayed or otherwise spatially distinguished. Exemplary bead-based arrays that can be used include, without limitation, a BeadChip™ Array available from Illumina, Inc. (San Diego, Calif.) or arrays such as those described in U.S. Pat. Nos. 6,266,459; 6,355,431; 6,770,441; 6,859,570; or 7,622,294; or PCT Publication No. WO 00/63437, each of which is incorporated herein by reference. Beads can be located at discrete locations, such as wells, on a solid-phase support, whereby each location accommodates a single bead. Alternatively, discrete locations where beads reside can each include a plurality of beads as described, for example, in U.S. Pat. App. Pub. Nos. 2004/0263923 A1, 2004/0233485 A1, 2004/0132205 A1, or 2004/0125424 A1, each of which is incorporated herein by reference.

As will be recognized from the above bead array embodiments, a method of the present disclosure can be carried out in a multiplex format whereby multiple different analytes (e.g. different types of nucleic acids) are detected in parallel in a method set forth herein. Although it is also possible to serially process different types of nucleic acids using one or more steps of the methods set forth herein, parallel processing can provide cost savings, time savings and uniformity of conditions. An apparatus or method of the present disclosure can include at least 2, 10, 100, $1\times10^3$, $1\times10^4$, $1\times10^5$, $1\times10^6$, $1\times10^9$, or more different analytes. Alternatively or additionally, an apparatus or method of the present disclosure can include at most $1\times10^9$, $1\times10^6$, $1\times10^5$, $1\times10^4$, $1\times10^3$, 100, 10, 2 or fewer, different analytes. Accordingly, various reagents or products set forth herein as being useful in the apparatus or methods (e.g. primer-template nucleic acid hybrids or stabilized ternary complexes) can be multiplexed in these ranges.

Further examples of commercially available arrays that can be used include, for example, an Affymetrix GeneChip™ array. A spotted array can also be used according to some embodiments. An exemplary spotted array is a CodeLink™ Array available from Amersham Biosciences. Another array that is useful is one that is manufactured using inkjet printing methods such as SurePrint™ Technology available from Agilent Technologies.

Other useful arrays include those that are used in nucleic acid sequencing applications. For example, arrays that are used to attach amplicons of genomic fragments (often referred to as clusters) can be particularly useful. Examples of nucleic acid sequencing arrays that can be used herein include those described in Bentley et al., Nature 456:53-59 (2008), PCT Pub. Nos. WO 91/06678; WO 04/018497 or WO 07/123744; U.S. Pat. Nos. 7,057,026; 7,211,414; 7,315,019; 7,329,492 or 7,405,281; or U.S. Pat. App. Pub. No. 2008/0108082, each of which is incorporated herein by reference.

A method of the present disclosure can be carried out for one or more nucleic acid ensembles, an ensemble being a population of nucleotides having a common template sequence. Cluster methods can be used to attach one or more ensembles to a solid support. As such, an array can have a plurality of ensembles, each of the ensembles being referred to as a 'cluster,' 'array site' or 'array feature' in that format. Clusters can be formed using methods known in the art such as bridge amplification or emulsion PCR. Useful bridge amplification methods are described, for example, in U.S. Pat. No. 5,641,658 or 7,115,400; or U.S. Patent Pub. Nos. 2002/0055100 A1; 2004/0002090 A1; 2004/0096853 A1; 2007/0128624 A1; or 2008/0009420 A1. Emulsion PCR methods include, for example, methods described in Dressman et al., Proc. Natl. Acad. Sci. USA 100:8817-8822 (2003), WO 05/010145, or U.S. Patent Pub. Nos. 2005/0130173 A1 or 2005/0064460 A1, each of which is incorporated herein by reference in its entirety. Another useful method for amplifying nucleic acids on a surface to form a cluster is rolling circle amplification (RCA), for example, as described in Lizardi et al., Nat. Genet. 19:225-232 (1998) or US 2007/0099208 A1, each of which is incorporated herein by reference.

The nucleic acids that are located in a particular cluster or at a particular feature of an array can be monoclonal. Some or all of the clusters or features in an array can be monoclonal. However, clusters or array features need not be monoclonal. For example, one or more of the nucleic acids in a cluster or at a feature can differ from the majority of nucleic acids at the same cluster or feature. In particular configurations of the methods or apparatus herein, a small number of nucleic acid impurities can be acceptable since the majority of species at the cluster or feature can be detected with adequate confidence.

In particular embodiments, a nucleic acid or other assay component is attached to a flow cell surface or to a solid support in a flow cell. A flow cell allows convenient fluidic manipulation by passing solutions into and out of a fluidic chamber that contacts the support-bound, ternary complex. The flow cell also provides for detection of the fluidically manipulated components. For example, a detector can be positioned to detect signals from the solid support, such as signals from a label that is recruited to the solid support due to formation of a stabilized ternary complex or due to polymerase catalyzed incorporation of a labeled nucleotide into a primer-template hybrid that is attached to the support. Exemplary flow cells that can be used are described, for example, in US Pat. App. Pub. No. 2010/0111768 A1, WO 05/065814 or US Pat. App. Pub. No. 2012/0270305 A1, each of which is incorporated herein by reference.

Different activities of polymerases can be exploited in a method set forth herein. A polymerase can be useful, for example, to form a stabilized ternary complex and/or to extend a primer. The different activities can follow from differences in the structure (e.g. via natural activities, mutations or chemical modifications). Nevertheless, polymerase can be obtained from a variety of known sources and applied in accordance with the teachings set forth herein and recognized activities of polymerases. Useful DNA polymerases include, but are not limited to, bacterial DNA polymerases, eukaryotic DNA polymerases, archaeal DNA polymerases, viral DNA polymerases and phage DNA polymerases. Bacterial DNA polymerases include *E. coli* DNA polymerases I, II and III, IV and V, the Klenow fragment of *E. coli* DNA polymerase, *Clostridium stercorarium* (Cst) DNA polymerase, *Clostridium thermocellum* (Cth) DNA polymerase and *Sulfolobus solfataricus* (Sso) DNA polymerase. Eukaryotic DNA polymerases include DNA polymerases $\alpha$, $\beta$, $\gamma$, $\delta$, $\epsilon$, $\eta$, $\zeta$, $\lambda$, $\sigma$, $\mu$, and $k$, as well as the Revl polymerase (terminal deoxycytidyl transferase) and terminal deoxynucleotidyl transferase (TdT). Viral DNA polymerases include T4 DNA polymerase, phi-29 DNA polymerase, GA-1, phi-29-like DNA polymerases, PZA DNA polymerase, phi-15 DNA polymerase, Cpl DNA polymerase, Cpl DNA polymerase, T7 DNA polymerase, and T4 polymerase. Other useful DNA polymerases include thermostable and/or thermophilic DNA polymerases such as *Thermus aquaticus* (Taq) DNA polymerase, *Thermus filiformis* (Tfi) DNA polymerase, *Thermococcus* zilligi (Tzi) DNA polymerase, *Thermus thermophilus* (Tth) DNA polymerase, *Thermus* flavusu (Tfl) DNA polymerase, *Pyrococcus* woesei (Pwo) DNA polymerase, *Pyrococcus furiosus* (Pfu) DNA polymerase and Turbo Pfu DNA polymerase, *Thermococcus litoralis* (Tli) DNA polymerase, *Pyrococcus* sp. GB-D polymerase, *Thermotoga maritima* (Tma) DNA polymerase, *Bacillus stearothermophilus* (Bst) DNA polymerase, *Pyrococcus Kodakaraensis* (KOD) DNA polymerase, Pfx DNA polymerase, *Thermococcus* sp. JDF-3 (JDF-3) DNA polymerase, *Thermococcus* gorgonarius (Tgo) DNA polymerase, *Thermococcus* acidophilium DNA polymerase; *Sulfolobus acidocaldarius* DNA polymerase; *Thermococcus* sp. go N-7 DNA polymerase; Pyrodictium occultum DNA polymerase; *Methanococcus voltae* DNA polymerase; *Methanococcus thermoautotrophicum* DNA polymerase; *Methanococcus jannaschii* DNA polymerase; *Desulfurococcus* strain TOK DNA polymerase (D. Tok Pol); *Pyrococcus abyssi* DNA polymerase; *Pyrococcus horikoshii* DNA polymerase; *Pyrococcus islandicum* DNA polymerase; *Thermococcus fumicolans* DNA polymerase; *Aeropyrum pernix* DNA polymerase; and the heterodimeric DNA polymerase DP1/DP2. Engineered and modified polymerases also are useful in connection with the disclosed techniques. For example, modified versions of the extremely thermophilic marine archaea *Thermococcus* species 9° N (e.g., Therminator DNA polymerase from New England BioLabs Inc.; Ipswich, Mass.) can be used.

Useful RNA polymerases include, but are not limited to, viral RNA polymerases such as T7 RNA polymerase, T3 polymerase, SP6 polymerase, and Kll polymerase; Eukaryotic RNA polymerases such as RNA polymerase I, RNA polymerase II, RNA polymerase III, RNA polymerase IV, and RNA polymerase V; and Archaea RNA polymerase.

Another useful type of polymerase is a reverse transcriptase. Exemplary reverse transcriptases include, but are not limited to, HIV-1 reverse transcriptase from human immunodeficiency virus type 1 (PDB 1HMV), HIV-2 reverse transcriptase from human immunodeficiency virus type 2, M-MLV reverse transcriptase from the Moloney murine leukemia virus, AMV reverse transcriptase from the avian myeloblastosis virus, and Telomerase reverse transcriptase that maintains the telomeres of eukaryotic chromosomes.

A polymerase having an intrinsic 3'-5' proofreading exonuclease activity can be useful for some embodiments. Polymerases that substantially lack 3'-5' proofreading exonuclease activity are also useful in some embodiments, for example, in most sequencing embodiments. Absence of exonuclease activity can be a wild type characteristic or a characteristic imparted by a variant or engineered polymerase structure. For example, exo minus Klenow fragment is a mutated version of Klenow fragment that lacks 3'-5' proofreading exonuclease activity. Klenow fragment and its exo minus variant can be useful in a method or composition set forth herein.

In some configurations of a method, apparatus or composition set forth herein, a polymerase can be linked to an exogenous label. Moreover, a fractionally labeled population of polymerases can be used, wherein the population includes polymerases that are linked to a label that produces a characteristic signal and polymerases that do not produce the signal, for example, due to lacking the exogenous label A method or apparatus of the present disclosure can optionally employ optical detection. For example, an assay component, such as a nucleotide, can be luminescent due to intrinsic properties or due to an exogenous label. Accordingly, a luminescent assay component can be excited at a wavelength that causes luminescent emission. The luminescent emission will occur in a particular wavelength range such that detection of signals in that range will indicate that the luminescent assay component is present. When using a fractionally labeled mixture of assay components, a first subset of the assay components will produce a particular signal, for example, due to exogenous labels on the assay components, and a second subset of the assay components will not produce the signal. Taking the example of a sequencing assay that utilizes nucleotides having an exogenous luminescent label, a first subset of nucleotides that are cognates for a first base type can contain a luminescent label that emits a characteristic signal when excited with light at an appropriate wavelength. Other nucleotides in the first subset are also cognates for the first base type but will not produce the characteristic signal when excited with the same wavelength of light (i.e. dark nucleotides). Typically, the dark nucleotides will lack any exogenous labels. In some configurations, the dark nucleotides can include labels, albeit labels that do not produce the characteristic signal of the labeled nucleotides in the first subset when excited at the wavelength of light used to excite the labels of the first subset of nucleotides.

Particularly useful optical detection systems include those that are found in sub-systems or components of nucleic acid sequencing systems. Several such detection apparatus are configured for optical detection, for example, detection of luminescence signals. Accordingly, an optical detection system can include an excitation system configured to irradiate a sample of interest such as a sample present in an array or flow cell. The optical detection system can further include an emission system configured to detect luminescence from the sample. Detection of luminescence can be carried out using methods known in the art pertaining to nucleic acid arrays or nucleic acid sequencing. A luminophore can be detected based on any of a variety of luminescence properties including, for example, emission wavelength, excitation wavelength, fluorescence resonance energy transfer (FRET) intensity, quenching, anisotropy or lifetime.

Examples of detection apparatus and components thereof that can be used in a system or method herein are described, for example, in US Pat. App. Pub. No. 2010/0111768 A1 or U.S. Pat. Nos. 7,329,860; 8,951,781 or 9,193,996, each of which is incorporated herein by reference. Other detection apparatus include those commercialized for nucleic acid sequencing such as those provided by Illumina™, Inc. (e.g. HiSeq™, MiSeq™, NextSeq™, or NovaSeq™ systems), Life Technologies™ (e.g. ABI PRISM™, or SOLID™ systems), or Qiagen (e.g. Genereader™ system). Other useful detectors are described in U.S. Pat. Nos. 5,888,737; 6,175,002; 5,695,934; 6,140,489; or 5,863,722; or US Pat. Pub. Nos. 2009/0247414 A1, or 2010/0111768; or WO2007/123744, each of which is incorporated herein by reference in its entirety.

Although the apparatus and methods of the present disclosure are illustrated in the context of optical detection in several exemplary embodiments herein, it will be understood that other detection modalities can be used instead. For example, the detector can be an electronic detector (see, for example, US Pat. App. Pub. Nos. 2009/0026082 A1; 2009/0127589 A1; 2010/0137143 A1; or 2010/0282617 A1, each of which is incorporated herein by reference in its entirety, or the Ion Torrent™ systems commercially available from ThermoFisher, Waltham, Mass.). A FET detector can be used such as one or more of those described in U.S. Pat. App. Ser. No. 62/767,712; US Pat. App. Pub. Nos. 2017/0240962 A1, 2018/0051316 A1, 2018/0112265 A1, 2018/0155773 A1 or 2018/0305727 A1; or U.S. Pat. Nos. 9,164,053, 9,829,456, 10,036,064, or 10,125,391, each of which is incorporated herein by reference.

A method of the present disclosure can include a step of extending a primer by polymerase catalyzed addition of one or more nucleotides or by ligase catalyzed addition of one or more oligonucleotides. Such extension steps are used to advance the primer to the next position that is to be detected when sequencing the template. Typically, the primer is extended by one nucleotide during each sequencing cycle such that adjacent positions in the template can be read serially. As an alternative, extension can be carried out such that a variable number and/or type of nucleotide(s) is added during each cycle. Exemplary techniques that can be used for variable extension include, but are not limited to, those set forth in U.S. patent application Ser. No. 16/265,942, or U.S. Pat. No. 8,236,532 or 8,753,816, each of which is incorporated herein by reference.

In many configurations, the nucleotides that are added to the primer will be reversibly terminated. Accordingly, extension can be controlled such that no more than one nucleotide is added to the primer during each cycle because the extended primer is reversibly terminated. The reversibly terminated primer can then be deblocked and extended to achieve sequencing of the template along which the primer is incrementally extended.

Examples of reagents and conditions that can be used for a polymerase-based primer extension step include, for example, those set forth in U.S. Pat. App. Pub. Nos. 2017/0022553 A1; 2018/0044727 A1; 2018/0187245 A1; or 2018/0208983 A1, each of which is incorporated herein by reference. Other useful reagent and conditions for polymerase-based primer extension are set forth in Bentley et al., *Nature* 456:53-59 (2008), WO 04/018497; WO 91/06678; WO 07/123744; U.S. Pat. Nos. 7,057,026; 7,329,492; 7,211,414; 7,315,019 or 7,405,281, and US Pat. App. Pub. No. 2008/0108082 A1, each of which is incorporated herein by reference.

Typically, an extension step employed in a method set forth herein will result in addition of a nucleotide cognate for any base type that is expected to be present in a template nucleic acid. For example, primer extension can be carried out under conditions that result in incorporation of cognate nucleotides for all four base types that are present in DNA (e.g. adenine, thymine, guanine and cytosine) or RNA (e.g. adenine, uracil, guanine and cytosine). The different nucleotide types can be present simultaneously in an extension reaction, or they can participate in serial extension reactions. For example, some or all of the nucleotide types can be delivered simultaneously in a single extension reaction. Alternatively, different nucleotide types can be serially delivered (individually or in subsets) such that they are combined into a single extension reaction or such that serial extension reactions occur.

Nucleotides present in a prior step may cause unwanted nucleotide incorporation if carried over into an extension step. Thus, a wash step can be employed prior to a primer extension step to remove contaminating nucleotides. Optionally, free nucleotides may be removed by enzymes such as phosphatases, by chemical modification or by physical separation techniques.

A fractionally labeled population of molecules can be produced in any of a variety of ways. In some cases, one or more fractionally labeled populations can be produced prior to use in a method set forth herein. For example, one or more fractionally labeled population(s) of nucleotides, polymerases or nucleic acids can be produced in a manufacturing environment and the fractionally labeled population(s) can be shipped to an end user for use in the method. Alternatively, one or more fractionally labeled population(s) can be produced as a method is being performed. For example, one or more fractionally labeled population(s) of nucleotides, polymerases or nucleic acids can be formed by creating mixtures from a labeled stock and non-labeled stock, adding labels to a portion of a non-labeled stock, removing labels from a portion of a labeled stock, quenching labels for a portion of a labeled stock or the like.

Several exemplary techniques for creating fractionally labeled populations of molecules will be exemplified below in the context of fractionally labeled nucleotides. This is done for ease of explanation. It will be understood that fractionally labeled populations of other types of molecules can be produced using similar techniques.

In a particular configuration, a fluidic system can include two reservoirs for the cognates of a particular nucleic acid base. One of the reservoirs can contain labeled nucleotides that complement the particular base, the label producing a signal that is to be detected for a sequencing method. The other reservoir can contain nucleotides that complement the particular base but lack labels that produce the signal. The fluidic system can further include an optional mixing chamber that is downstream of the reservoirs and upstream of a flow cell or other vessel where sequencing reactions are performed. The fluidic system can be configured with valves that can be used to control the amount of labeled nucleotide and non-labeled nucleotide that is delivered to the mixing chamber to achieve the desired fraction of labeled nucleotide. The mixing chamber can optionally be configured to increase the rate of mixing for example by employing a stirring, shaking or fluid toggling mechanism. In some cases, mixing of the nucleotides occurs in the flow cell or in fluid lines upstream of the flow cell. As such, a separate mixing chamber may not be needed.

In another configuration, a fluidic system can include two reservoirs for the cognates of a particular nucleic acid base: a first reservoir that contains labeled nucleotides that complement the particular base and a second reservoir containing nucleotides that complement the particular base but lack any labels that produce the signal of the labeled nucleotides. However, a separate mixing chamber need not be present. Rather, as a sequencing run proceeds, labeled nucleotides from the first reservoir can be added to the second reservoir. Thus, as the run proceeds, the fraction of labeled nucleotides in the second reservoir will increase, such that delivery of nucleotide from the second reservoir to a flow cell (or other vessel) will effectively result in an increase of the fraction of labeled nucleotide as the run proceeds.

Another configuration for delivery of fractionally labeled population(s) of nucleotides to a flow cell (or other vessel), can use a fluidic system that includes a first reservoir having non-labeled nucleotides and a second reservoir having reagents that can be used to label the nucleotides in the first reservoir. For example, the first reservoir can include nucleotides having a ligand (such as biotin) and the second reservoir can include labeled receptor molecules (e.g. labeled avidin or labeled streptavidin). Increasing amounts of labeled receptor molecules can be mixed with ligand-containing nucleotides to increase the fractional labeling of the nucleotides. Other chemistries can be used with this type of fluidic system. For example, the first reservoir can contain nucleotides having a first moiety that is covalently reactive with a second moiety (e.g. via click chemistry) and the second reservoir can include labels that have the second moiety. The nucleotides can be mixed with the labels and allowed to create covalent linkages of the labels to the nucleotides. The labeling chemistry can occur in a mixing chamber upstream of a flow cell (or other vessel) where sequencing chemistry is carried out, in fluid lines upstream of the flow cell (or other vessel) or in the flow cell (or other vessel).

As an alternative or addition to adding labels to nucleotides, labels can be removed or quenched to achieve different levels of fractional labeling. The early cycles of a sequencing reaction can use little to no label quenching or removal, whereas later cycles can employ a higher level of label quenching or removal. For example, a first reservoir can contain labeled nucleotides, the label producing a signal that is to be detected for a sequencing method, and a second reservoir can contain a quencher that reduces the signal. In another example, a first reservoir can contain labeled nucleotides, the label being attached to the nucleotide by a cleavable linker, and a second reservoir can contain a cleaving agent that cleaves the linker to remove the label from the nucleotide. Quenchers or cleavage agents can be mixed with the nucleotide in a chamber upstream of the flow cell (or other vessel) where sequencing is carried out. Alternatively, quencher or cleaving agent can contact the nucleotides in a fluid line or in the flow cell (or other vessel) where sequencing chemistry occurs.

For assay methods that utilize serial delivery of fractionally labeled mixtures of assay components, the fraction of labeled components in the mixtures can be cumulatively increased as the method proceeds. For example, the fraction of labeled nucleotides (compared to nucleotides that do not produce signals that are characteristic of the label) in the mixtures that are used for a sequencing method can be cumulatively increased over at least 2, 3, 5, 10, 25, 50, 100 or more cycles of the sequencing method. The increase in the faction of labeled nucleotides in the mixtures can occur for every cycle of a sequencing method. Alternatively, each increase can occur after several cycles have occurred. For example, the fraction of labeled nucleotides in the mixtures that are used for a sequencing method can be cumulatively increased after every 2, 3, 4, 5, 10, 25, 50 or 100 cycles. Similar schedules of fractional label increase can be used for assay components other than nucleotides and for assays other than sequencing nucleic acids.

The rate of change for the increase in the fraction of labeled nucleotides need not be consistent across the run. For example, the rate of change can accelerate as the run proceeds. For example, a first fractionally labeled mixture of nucleotides can be used for more cycles in the early part of a sequencing run compared to the number of cycles that use a second mixture of the fractionally labeled nucleotides later in the sequencing run, wherein the fraction of labeled nucleotides is increased in the second mixture compared to the first mixture. By way of more specific example of this acceleration, the fraction of labeled nucleotides in the mixtures that are used for a sequencing method can be cumulatively increased after the first 10 cycles, then after the next 8 cycles, then after the next 6 cycles, etc., optionally until the increase occurs after every cycle in the later part of the sequencing run. In an alternative example, the rate of change for the increase in the fraction of labeled nucleotides can decelerate as the run proceeds. Thus, a first fractionally labeled mixture of nucleotides can be used for fewer cycles in the early part of a sequencing run compared to the number of cycles that use a second fractionally labeled mixture of nucleotides later in the sequencing run, wherein the fraction of labeled nucleotide types is increased in the second mixture compared to the first mixture. By way of more specific example of this deceleration, the fraction of labeled nucleotides in the mixtures that are used for a sequencing method can be cumulatively increased after the first 2 cycles, then after the next 4 cycles, then after the next 6 cycles, etc.

Any of a variety of acceleration or deceleration schedules can be used when increasing the fraction of labeled assay components used in a method set forth herein. A particularly useful step schedule will match the rate of signal decay observed for a reference sequencing run that uses a fixed fraction of labeled nucleotides across the cycles. The reference sequencing run can be an empirical run or a theoretically modeled run. As such the rate of increase in fractional labeling can offset the rate of signal decay that would occur absent the use of an increasing fraction of labeled nucleotides. For example, if a sequencing run is prone to exponential signal decay then the fraction of labeled nucleotides can increase exponentially over the run. Similarly, the fraction of labeled nucleotides can be increased geometrically when a sequencing method is prone to a geometric rate of signal decay. The fraction of labeled nucleotides can be linearly increased when a sequencing method is prone to a linear rate of signal decay.

The fraction of labeled assay components can be increased according to a predefined schedule, for example, a predefined schedule that is based on predicted rates of signal decay for the assay. Alternatively, the rate of increase for the fraction of labeled assay components can be determined from real time observation of the rate of signal decay for the assay. Accordingly, an apparatus or method set forth herein can include a feedback mechanism, whereby the fraction of labeled assay components is increased at a particular cycle upon observation of a drop in signal (or increase in signal decay) for a prior cycle or upon observation of other characteristics of the assay that are indicative of a potential drop in signal (or increase in signal decay).

The present disclosure provides apparatus for processing and detecting analytes of interest, for example, using methods set forth herein. For example, an apparatus of the present disclosure can be configured to contain fluidic components that deliver fractionally labeled assay components to a sample and detection components to observe interactions between the sample and assay components, or products of the interactions. The fluidics components can optionally include reservoirs for storing fluidic assay components, a mixing chamber, a reaction vessel where a sample of interest can react with the fluidic assay components, a pressure source or other driving force for moving fluids, a path for moving fluids, valves or other selectors for gating or directing fluids through the path, and/or a waste reservoir for spent fluids.

The number and volume of reservoirs in an apparatus of the present disclosure can be selected to accommodate one or more of the assay configurations set forth herein. Taking a nucleic acid sequencing apparatus as an example, the apparatus can optionally include reservoirs for assay components such as nucleotides, polymerases, nucleic acids, deblocking reagents, wash solutions and the like. A single reservoir can contain a fractionally labeled population of a particular assay component. Returning to the example of a sequencing apparatus, a reservoir can contain a fractionally labeled mixture of nucleotides wherein the nucleotides in the reservoir are cognates for a common base. In some configurations, a single reservoir contains fractionally labeled mixture of nucleotide cognates for several types of bases expected to be present in a template nucleic acid. Alternatively, separate reservoirs can be provided, each reservoir dedicated to storing a fractionally labeled mixture of nucleotide cognates for a single type of base expected to be present in a template nucleic acid.

In some configurations, a labeled assay component of one type can be stored in a first reservoir and a dark assay component of that type can be stored in a second reservoir. The labeled and dark assay components can be mixed to form a fractionally labeled population of the assay components. For example, the labeled and dark assay components can be delivered separately to a reaction vessel that houses a sample that is to be observed. As such, mixing can occur in the reaction vessel. Alternatively, mixing of the labeled and dark assay components can occur in a mixing chamber that is upstream of the reaction vessel. For example, the labeled and dark assay components can be delivered separately to the mixing chamber, allowed to mix to form a fractionally labeled population of assay components, and then the fractionally labeled population of assay components can be delivered to the reaction vessel (i.e. the labeled and dark assay components can be delivered to the reaction vessel as a mixture).

An advantage of storing labeled and dark assay components of a particular type in separate reservoirs is the ability to produce a plurality of populations of assay components that differ from each other in the fraction of labeled components to dark components. Accordingly, a plurality of different fractionally labeled populations can be provided by only two reservoirs as opposed to the large plurality of reservoirs that would otherwise be required to hold premixed versions of the fractionally labeled populations. A further advantage of mixing the labeled and dark assay components from separate reservoirs is that the fractions of labeled and dark assay components need not be pre-determined. As such, the fraction that is to be delivered in a given cycle of an assay can be determined from empirical analysis of previous cycles and the quantity of labeled assay component and dark assay component to be drawn from each reservoir can be adjusted accordingly.

In some configurations of SBB™ sequencing, dark nucleotides are used for two different steps per cycle. More specifically, a dark nucleotide can be included in a fractionally labeled mixture of nucleotides that is used for an examination step and a dark nucleotide can be used for an extension step. The dark nucleotides will function as cognates for the same base type in both steps. Thus, a single type of dark nucleotide can be used and it can be stored in a single reservoir that is used for both steps. In some configurations, the dark nucleotide that is used for the extension step will include a reversible terminator moiety. This is useful for preventing more than one nucleotide from being incorporated into the primer in the extension step and for producing a reversibly terminated primer that will not be extended during the subsequent examination step. The dark nucleotide that is used for the examination step need not include a reversible terminator since the nucleotide is not incorporated under the ternary complex stabilization conditions typically employed for examination. However, a reversible terminator can be present in many configurations of the method since it does not interfere with formation and examination of a stabilized ternary complex. Thus, the dark nucleotide that is present in a fractionally labeled mixture of nucleotides can include a reversible terminator moiety. The presence of the reversible terminator on the dark nucleotide can provide the added benefit of capping a primer from further extension should it be inadvertently added to an extendable primer during the examination step or should it be inadvertently carried over to a subsequent extension step. This in turn, can help guard against phasing errors in an SBB™ sequencing procedure.

Any of a variety of reaction vessels can be included in an apparatus of the present disclosure. Particularly useful vessels include flow cells such as those set forth herein in the context of nucleic acid sequencing methods. Other vessels can be used including, for example, a multiwell plate, petri dish, microscope slide, microarray cartridge, cuvette, field-effect transistor (FET) or the like.

Fluids can be manipulated in an apparatus herein using fluidic components known in the art including, for example, those employed in nucleic acid sequencing platforms set forth herein. For example, microfluidic systems can include tubing, channels or other fluidic lines to move the fluids. The fluids can be moved via positive or negative pressure, for example, produced by a syringe pump, peristaltic pump, Takasago pump, linear displacement pump, solenoid operated pump or the like. Any of a variety of valves can be used to select which fluidic components will flow to what location in the apparatus including, for example, a rotary valve, linear valve, solenoid valve or the like.

An alternative fluidic system that can be useful is one that utilizes a droplet actuator. An exemplary droplet actuator will move fluid droplet via electrowetting-mediated operations. For examples of droplet actuators, see U.S. Pat. Nos. 6,565,727; 6,773,566; 6,911,132; 6,977,033; 7,163,612; 7,547,380; or 7,641,779; or U.S. Pat. App. Pub. No. 2003/0205632 A1; 2005/0179746; 2006/0164490 A1; 2006/0194331 A1; 2007/0023292 A1; 2008/0124252 A1; 2009/0192044 A1; 2009/0283407 A1; 2009/0321262 A1; or 2010/0096266 A1, each of which is incorporated herein be reference.

Any of a variety of detection components can be configured for use in an apparatus set forth herein. Examples include luminescence detectors, surface plasmon resonance detectors and others known in the art. Exemplary systems having fluidic and detection components that can be readily modified for use in a system herein include, but are not limited to, those set forth herein in the context of nucleic acid sequencing methods.

Optionally, an apparatus of the present disclosure can be networked to or can include a computer processing unit (CPU) that is configured to operate components of the apparatus. For example, the CPU can be programmed with a schedule for increasing the fraction of labeled assay components in a fractionally labeled population of assay components. The same or different CPU can interact with the apparatus to acquire, store and process signals (e.g. signals detected in a method set forth herein). In particular embodiments, a CPU can be used to determine, from the signals, the identity of the nucleotide that is present at a particular location in a template nucleic acid. In some cases, the CPU will identify a sequence of nucleotides for the template from the signals that are detected. In particular embodiments, the CPU is programmed to identify signal decay or some other characteristic of an assay that suggests a benefit for altering the fraction of labeled assay components in a fractionally labeled population of assay components.

A useful CPU can include one or more of a personal computer system, server computer system, thin client, thick client, hand-held or laptop device, multiprocessor system, microprocessor-based system, set top box, programmable consumer electronic, network PC, minicomputer system, mainframe computer system, smart phone, distributed cloud computing environments that include any of the above systems or devices, or the like. The CPU can include one or more processors or processing units, a memory architecture that may include RAM and non-volatile memory. The memory architecture may further include removable/non-removable, volatile/non-volatile computer system storage media. Further, the memory architecture may include one or more readers for reading from and writing to a non-removable, non-volatile magnetic media, such as a hard drive, a magnetic disk drive for reading from and writing to a removable, non-volatile magnetic disk, and/or an optical disk drive for reading from or writing to a removable, non-volatile optical disk such as a CD-ROM or DVD-ROM. The CPU may also include a variety of computer system readable media. Such media may be any available media that is accessible by a cloud computing environment, such as volatile and non-volatile media, and removable and non-removable media.

The memory architecture may include at least one program product having at least one program module implemented as executable instructions that are configured to carry out one or more steps of a method set forth herein. For example, executable instructions may include an operating system, one or more application programs, other program modules, and program data. Generally, program modules may include routines, programs, objects, components, logic, data structures, and so on, that perform particular tasks set forth herein.

The components of a CPU may be coupled by an internal bus that may be implemented as one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

A CPU can optionally communicate with one or more external devices such as a keyboard, a pointing device (e.g. a mouse), a display, such as a graphical user interface (GUI), or other device that facilitates interaction of a use with the nucleic acid detection system. Similarly, the CPU can communicate with other devices (e.g., via network card, modem, etc.). Such communication can occur via I/O interfaces. Still yet, a CPU of a system herein may communicate with one or more networks such as a local area network (LAN), a general wide area network (WAN), and/or a public network (e.g., the Internet) via a suitable network adapter.

Sequencing by Binding™ Methods and Related Use Cases

The present disclosure provides a method for sequencing a population of primer-template nucleic acid hybrids, wherein the templates share a common sequence. The method can include steps of: (a) binding the population of primer-template nucleic acid hybrids with a fractionally labeled mixture of nucleotides, thereby forming a fractionally labeled population of primer-template nucleic acid hybrids that are non-covalently bound to nucleotides via stabilized ternary complexes, wherein the mixture includes nucleotide cognates for a common base type in the templates, and wherein a fraction of the nucleotide cognates for the common base type in the mixture are exogenously labeled nucleotides that produce a signal that is not produced by other nucleotide cognates for the common base type in the mixture; (b) detecting the signal from the fractionally labeled population of primer-template nucleic acid hybrids that are non-covalently bound to nucleotides via the stabilized ternary complexes; (c) adding a nucleotide to each of the primers of the primer-template nucleic acid hybrids, whereby the primers of the primer-template nucleic acid hybrids are extended to a subsequent position in the common sequence of the templates, and (d) repeating (a) through (c), wherein the mixture is replaced with a second mixture of the fractionally labeled nucleotides, wherein the fraction of the exogenously labeled nucleotides is higher in the second mixture compared to the mixture and wherein the primer-template nucleic acid hybrids comprise the extended primers.

The present disclosure further provides a method for sequencing a population of nucleic acids that includes subjecting a population of primer-template nucleic acid hybrids to multiple cycles of a nucleic acid sequencing process, wherein the templates share a common sequence, wherein each of the cycles includes steps of: (a) forming a mixed population including primer-template nucleic acid hybrids that are bound to a first nucleotide type and primer-template nucleic acid hybrids that are bound to a second nucleotide type, wherein the nucleotides are noncovalently bound to the primer-template nucleic acid hybrids via stabilized ternary complexes, wherein the first nucleotide type has an exogenous label that produces a first signal and wherein the second nucleotide type is substantially devoid of labels that produce the first signal, wherein the first and second nucleotide types are cognates for the same base type in the template; (b) detecting the signal from the stabilized ternary complexes in the mixed population, and (c) adding a nucleotide to each of the primers of the primer-template nucleic acid hybrids, wherein the fraction of the first nucleotide type compared to the second nucleotide type is increased in the mixed population over at least two of the cycles of the nucleic acid sequencing process. Optionally, each of the cycles can include dissociating the ternary complexes prior to the adding of the nucleotide to each of the primers.

An example of a nucleic acid sequencing process that can be modified to use a fractionally labeled mixture of nucleotides is a Sequencing By Binding™ (SBB™) reaction. Embodiments of the methods exploit the specificity with which a polymerase can form a stabilized ternary complex with a primer-template nucleic acid hybrid and a next correct nucleotide. The next correct nucleotide can be non-covalently bound to the stabilized ternary complex, interacting with the other members of the complex solely via non-covalent interactions. Any number of SBB™ configurations can be modified to provide one or more of the advantages set forth herein. Exemplary configurations that can be modified are described in commonly owned US Pat. App. Pub. Nos. 2017/0022553 A1; 2018/0044727 A1; 2018/0187245 A1; or 2018/0208983 A1, each of which is incorporated herein by reference. Generally, SBB™ methods for determining the sequence of a template nucleic acid molecule can be based on formation of a ternary complex (between polymerase, primed nucleic acid and cognate nucleotide) under specified conditions. The method can include an examination phase followed by a nucleotide incorporation phase. The examination phase can be modified to use one or more mixtures of fractionally labeled nucleotides. The fraction of labeled nucleotides, compared to dark nucleotides, can be increased over multiple cycles of the run.

The examination phase of an SBB™ process can be carried out in a flow cell, the flow cell containing at least one template nucleic acid molecule primed with a primer, by delivering reagents to form a first reaction mixture in the flow cell. The reaction mixture can include the primed template nucleic acid, a polymerase and a fractionally labeled mixture of nucleotides that are cognates for a common nucleotide type. Interaction of polymerase and a nucleotide with the primed template nucleic acid molecule can be observed under conditions where the nucleotide is not covalently added to the primer; and the next base in each template nucleic acid can be identified using the observed interaction of the polymerase and nucleotide with the primed template nucleic acid molecule. The interaction between the primed template, polymerase and nucleotide can be detected in a variety of schemes appropriate to the label that is present in the fractionally labeled mixture of nucleotides.

During the examination phase of an SBB™ process, discrimination between correct and incorrect nucleotides can be facilitated by ternary complex stabilization. A variety of conditions and reagents can be useful to stabilize a ternary complex. For example, the primer can contain a reversible blocking moiety that prevents covalent attachment of nucleotide; and/or cofactors that are required for extension, such as divalent metal ions, can be absent; and/or non-catalytic metal ions, such as inhibitory divalent cations that inhibit polymerase-based primer extension, can be present; and/or the polymerase that is present in the examination phase can have a chemical modification and/or mutation that inhibits primer extension; and/or the nucleotides can have chemical modifications that inhibit incorporation, such as 5' modifications that remove or alter the native triphosphate moiety.

While a ternary complex can form between a polymerase, primer-template nucleic acid hybrid and next correct nucleotide in the absence of certain catalytic metal ions (e.g., $Mg^{2+}$), chemical addition of the nucleotide is inhibited in the absence of the catalytic metal ions. Low or deficient levels of catalytic metal ions causes non-covalent sequestration of the next correct nucleotide in a stabilized ternary complex. Other methods disclosed herein also can be used to produce a stabilized ternary complex.

Optionally, a stabilized ternary complex can be formed when the primer of the primer-template nucleic acid hybrid includes a blocking moiety (e.g. a reversible terminator moiety) that precludes enzymatic incorporation of an incoming nucleotide into the primer. The interaction can take place in the presence of stabilizers, whereby the polymerase-nucleic acid interaction is stabilized in the presence of the next correct nucleotide. The primer of the primer-template nucleic acid hybrid optionally can be either an extendible primer, or a primer blocked from extension at its 3'-end (e.g., blocking can be achieved by the presence of a reversible terminator moiety on the 3'-end of the primer). The primer-template nucleic acid hybrid, the polymerase and the cognate nucleotide are capable of forming a stabilized ternary complex when the base of the cognate nucleotide is complementary to the next base of the primer-template nucleic acid hybrid.

As set forth above, conditions that favor or stabilize a ternary complex can be provided by the presence of a blocking group that precludes enzymatic incorporation of an incoming nucleotide into the primer (e.g. a reversible terminator moiety on the 3' nucleotide of the primer) or the absence of a catalytic metal ion. Other useful conditions include the presence of a ternary complex stabilizing agent such as a non-catalytic ion (e.g., a divalent or trivalent non-catalytic metal ion) that inhibits nucleotide incorporation or polymerization. Non-catalytic metal ions include, but are not limited to, calcium, strontium, scandium, titanium, vanadium, chromium, iron, cobalt, nickel, copper, zinc, gallium, germanium, arsenic, selenium, rhodium, europium, and terbium ions. Optionally, conditions that disfavor or destabilize binary complexes (i.e. complexes between polymerase and primed nucleic acid but lacking cognate nucleotide) are provided by the presence of one or more monovalent cations and/or glutamate anions. As a further option, a polymerase engineered to have reduced catalytic activity or reduced propensity for binary complex formation can be used.

As set forth above, ternary complex stabilization conditions can accentuate the difference in affinity of polymerase toward primer-template nucleic acid hybrids in the presence of different nucleotides, for example, by destabilizing binary complexes. Optionally, the conditions cause differential affinity of the polymerase for the primer-template in the presence of different nucleotides. By way of example, the conditions include, but are not limited to, high salt and glutamate ions. For example, the salt may dissolve in aqueous solution to yield a monovalent cation, such as a monovalent metal cation (e.g., sodium ion or potassium ion). Optionally, the salt that provides the monovalent cations (e.g., monovalent metal cations) further provides glutamate ions. Optionally, the source of glutamate ions can be potassium glutamate. In some instances, the concentrations of potassium glutamate that can be used to alter polymerase affinity of the primer-template hybrid extend from 10 mM to 1.6 M of potassium glutamate, or any amount in between 10 mM and 1.6 M. As indicated above, high salt refers to a concentration of salt from 50 to 1,500 mM salt.

It will be understood that options set forth herein for stabilizing a ternary complex need not be mutually exclusive and instead can be used in various combinations. For example, a ternary complex can be stabilized by one or a combination of means including, but not limited to, cross-linking of the polymerase domains, crosslinking of the polymerase to the nucleic acid, polymerase mutations that stabilize the ternary complex, allosteric inhibition by small molecules, uncompetitive inhibitors, competitive inhibitors, non-competitive inhibitors, absence of catalytic metal ions, presence of a blocking moiety on the primer, and other means set forth herein.

A stabilized ternary complex can include a native nucleotide, nucleotide or modified nucleotide as desired to suit a particular application or configuration of the methods. The nucleotides may be non-incorporable nucleotides (i.e. nucleotides that are incapable of reacting with the 3' oxygen of a primer to form a covalent linkage). Nucleotides that participate in stabilized ternary complexes can include terminators that reversibly prevent subsequent nucleotide incorporation at the 3'-end of the primer after the nucleotide has been incorporated into the primer. In certain embodiments, a reversible terminator moiety can be removed from a primer, in a process known as "deblocking," allowing for subsequent nucleotide incorporation.

In some embodiments, a nucleotide that participates in forming a ternary complex can include an exogenous label. For example, an exogenously labeled nucleotide can include a reversible or irreversible terminator moiety, an exogenously labeled nucleotide can be non-incorporable, an exogenously labeled nucleotide can lack terminator moieties, an exogenously labeled nucleotide can be incorporable or an exogenously labeled nucleotide can be both incorporable and non-terminated. Labeled nucleotides can be useful when present in a fractionally labeled mixture of nucleotides.

Alternatively or additionally, a nucleotide that participates in forming a ternary complex can lack exogenous labels (i.e. the nucleotide can be "non-labeled"). For example, a non-labeled nucleotide can include a reversible or irreversible terminator moiety, a non-labeled nucleotide can be non-incorporable, a non-labeled nucleotide can lack terminator moieties, a non-labeled nucleotide can be incorporable or a non-labeled nucleotide can be both incorporable and non-terminated. Non-labeled nucleotides can be useful when present in a fractionally labeled mixture of nucleotides or when a label on a polymerase is used to detect a stabilized ternary complex. Non-labeled nucleotides can also be useful in an extension step of a method set forth herein. It will be understood that absence of a moiety or function for a nucleotide refers to the nucleotide having no such function or moiety. It will also be understood that one or more of the functions or moieties set forth herein for a nucleotide, or analog thereof, or otherwise known in the art for a nucleotide, or analog thereof, can be specifically omitted in a method or composition set forth herein.

In particular embodiments, the primer strand of a primer-template hybrid molecule that is present in a stabilized ternary complex is chemically unchanged by the polymerase that is present during one or more steps of a method set forth herein. For example, the primer need not be extended by formation of a new phosphodiester bond, nor shortened by nucleolytic degradation during a step for forming a stabilized ternary complex, nor during a step for detecting the stabilized ternary complex.

Any of a variety of polymerases can be used to form a stabilized ternary complex in a method set forth herein. Polymerases that may be used include naturally occurring polymerases and modified variations thereof, including, but not limited to, mutants, recombinants, fusions, genetic modifications, chemical modifications, synthetics, and analogs. Naturally occurring polymerases and modified variations thereof are not limited to polymerases that have the ability to catalyze a polymerization reaction. Optionally, the naturally occurring and/or modified variations thereof have the ability to catalyze a polymerization reaction in at least one condition that is not used during formation or examination of a stabilized ternary complex. Optionally, the naturally-occurring and/or modified variations that participate in stabilized ternary complexes have modified properties, for example, enhanced binding affinity to nucleic acids, reduced binding affinity to nucleic acids, enhanced binding affinity to nucleotides, reduced binding affinity to nucleotides, enhanced specificity for next correct nucleotides, reduced specificity for next correct nucleotides, reduced catalysis rates, catalytic inactivity etc. Mutant polymerases include, for example, polymerases wherein one or more amino acids are replaced with other amino acids, or insertions or deletions of one or more amino acids. Exemplary polymerase mutants that can be used to form a stabilized ternary complex include, for example, those set forth in US Pat. App. Pub. Nos. 2018/0155698 A1 or 2017/0314072 A1, each of which is incorporated herein by reference.

Modified polymerases include polymerases that contain an exogenous label moiety (e.g., an exogenous fluorophore), which can be used to detect the polymerase. Optionally, the label moiety can be attached after the polymerase has been at least partially purified using protein isolation techniques. For example, the exogenous label moiety can be chemically linked to the polymerase using a free sulfhydryl or a free amine moiety of the polymerase. This can involve chemical linkage to the polymerase through the side chain of a cysteine residue, or through the free amino group of the N-terminus. An exogenous label moiety can also be attached to a polymerase via protein fusion. Exemplary label moieties that can be attached via protein fusion include, for example, green fluorescent protein (GFP), phycobiliproteins (e.g. phycocyanin and phycoerythrin) or wavelength-shifted variants of GFP or phycobiliproteins. In some embodiments, an exogenous label on a polymerase can function as a member of a FRET pair. The other member of the FRET pair can be an exogenous label that is attached to a nucleotide that binds to the polymerase in a stabilized ternary complex. As such, the stabilized ternary complex can be detected or identified via FRET. A method of the present disclosure can employ a fractionally labeled mixture of polymerases. As such a first subset of the polymerases used in an examination step can be attached to a label that produces a characteristic signal and a second subset of the polymerases can be substantially devoid of labels that produce the characteristic signal.

Alternatively, a polymerase that participates in a stabilized ternary complex need not be attached to an exogenous label. For example, the polymerase need not be covalently attached to an exogenous label. Instead, the polymerase can lack any label until it associates with a labeled nucleotide and/or labeled nucleic acid (e.g. labeled primer and/or labeled template).

After an examination step, any reversible terminator moiety present on the 3'-nucleotide of a primer can be removed so that the primer of the primed template nucleic acid can participate in phosphodiester bond formation. Any of a variety of deblocking reagents and methods can be used that is suitable for the reversible terminator moiety used. Examples are set forth in U.S. Pat. App. Pub. Nos. 2008/0108082 A1, 2017/0022553 A1, 2018/0044727 A1, 2018/0187245 A1, or 2018/0208983 A1; Bentley et al., *Nature* 456:53-59 (2008); WO 04/018497; WO 91/06678; WO 07/123744; or U.S. Pat. Nos. 7,057,026; 7,329,492; 7,211,414; 7,315,019 7,405,281, 7,544,794 or 8,034,923 each of which is incorporated herein by reference The extension phase can then be carried out by creating conditions in the flow cell where a nucleotide can be added to the primer on each template nucleic acid molecule. In some embodiments, this involves removal of reagents used in the examination phase and replacing them with reagents that facilitate extension. For example, examination reagents can be replaced with a polymerase and nucleotide(s) that are capable of extension. Alternatively, one or more reagents can be added to the examination phase reaction to create extension conditions. For example, catalytic divalent cations can be added to an examination mixture that was deficient in the cations, and/or polymerase inhibitors can be removed or disabled, and/or extension competent nucleotides can be added, and/or a deblocking reagent can be added to render primer(s) extension competent, and/or extension competent polymerase can be added.

A primer extension step can be carried out by contacting a primer-template nucleic acid hybrid with an extension reaction mixture. In some cases, the fluid that was present in a previous step (e.g. in a prior detection or examination step) is removed and replaced with the extension reaction mixture. Alternatively, the extension reaction mixture can be formed by adding one or more reagents to the fluid that was present in a detection or examination step. Optionally, the extension reaction mixture includes a different composition of nucleotides than a previous step such as a previous examination step. For example, an examination step can include a fractionally labeled mixture of nucleotides that are not present in the extension reaction. Optionally, the nucleotide that is added to each of the primers is substantially incapable of producing a characteristic signal that is used for detecting ternary complexes during an examination step. For example, the nucleotide that is added to each of the primers can be substantially devoid of exogenous labels.

Optionally, a nucleotide bound within a stabilized ternary complex during an examination step is then incorporated into the 3'-end of a primer during a subsequent primer extension step. Alternatively, a primer extension step includes replacing a nucleotide from a prior examination step and incorporating another nucleotide (of the same or different type) into the 3'-end of the primer.

In some embodiments, a dark nucleotide that is reversibly terminated is carried over from an examination step to a primer extension step. For example, a reversibly terminated dark nucleotide that is included in a fractionally labeled mixture of nucleotides can be carried over from an examination step to a subsequent primer extension step.

Optionally, a polymerase present during an examination step is removed and replaced with a different polymerase for a subsequent primer extension step. Alternatively, the polymerase present during the examination step is retained and modified for a subsequent incorporation step. Optionally, one or more nucleotides present during an examination step are modified for a subsequent primer extension step. A fluid, reagent or condition that is present during an examination step may be altered by any of a variety of techniques for use in a subsequent primer extension step. Exemplary techniques include, but are not limited to, removing reagents, chelating reagents, diluting reagents, adding reagents, altering reaction conditions such as temperature, ionic strength, conductivity or pH, or any combination thereof. The reagents in a reaction mixture including any combination of polymerase, primed template nucleic acid, and nucleotide may be modified during an examination step and/or primer extension step.

Washes can be carried out between the various delivery steps of an SBB™ process. For example, a wash step can be useful for separating a primed template nucleic acid from other reagents, such as nucleotides from a fractionally labeled mixture of nucleotides, that were contacted with the primed template nucleic acid under ternary complex stabilizing conditions during an SBB™ process. Such a wash can remove one or more reagents from interfering with examination of a first reaction mixture or from contaminating a second reaction mixture that is to be formed on a substrate (or in a vessel) that had previously been in contact with the first reaction mixture. For example, a primed template nucleic acid can be contacted with a polymerase and a fractionally labeled mixture of nucleotides to form a first reaction mixture under ternary complex stabilizing conditions, and the first reaction mixture can be examined. Optionally, a wash can be carried out prior to examination to remove reagents that are not participating in formation of a stabilized ternary complex such as excess nucleotides from a fractionally labeled mixture of nucleotides. Alternatively or additionally, a wash can be carried out after the examination step to remove one or more component of the first reaction mixture from the primed template nucleic acid. For example the wash can remove nucleotides from a fractionally labeled mixture of nucleotides of a first type to form reaction mixture under ternary complex stabilizing conditions. Then the primed template nucleic acid can be contacted with a polymerase and a fractionally labeled mixture of nucleotides of a second type to form a second reaction mixture under ternary complex stabilizing conditions, and the second reaction mixture can be examined for ternary complex formation. As before, an optional wash can be carried out prior to the second examination to remove the nucleotides of the first type that are not participating in formation of a stabilized ternary complex.

Sequencing by Synthesis Methods and Related Use Cases

The present disclosure provides a method for sequencing a population of primer-template nucleic acid hybrids, wherein the templates share a common sequence. The method can include steps of: (a) binding the population of primer-template nucleic acid hybrids with a fractionally labeled mixture of nucleotides, thereby forming a fractionally labeled population of primer-template nucleic acid hybrids, wherein the nucleotides are covalently bound to the primers via polymerase catalyzed primer extension, wherein the mixture includes nucleotide cognates for a common base type in the templates, and wherein a fraction of the nucleotide cognates for the common base type in the mixture are exogenously labeled nucleotides that produce a signal that is not produced by other nucleotide cognates for the common base type in the mixture; (b) detecting the signal from the fractionally labeled population of primer-template nucleic acid hybrids; and (c) repeating (a) and (b), wherein the mixture is replaced with a second mixture of the fractionally labeled nucleotides, wherein the fraction of the exogenously labeled nucleotides is higher in the second mixture compared to the mixture. Optionally, the polymerase is removed from the fractionally labeled population prior to (b).

The present disclosure further provides a method for sequencing a population of nucleic acids that includes subjecting a population of primer-template nucleic acid hybrids to multiple cycles of a nucleic acid sequencing process, wherein the templates share a common sequence, wherein each of the cycles includes steps of: (a) forming a mixed population including primer-template nucleic acid hybrids that are bound to a first nucleotide type and primer-template nucleic acid hybrids that are bound to a second nucleotide type, wherein the nucleotides are covalently bound to the primers via polymerase catalyzed primer extension, wherein the first nucleotide type has an exogenous label that produces a first signal and wherein the second nucleotide type is substantially devoid of labels that produce the first signal, wherein the first and second nucleotide types are cognates for the same base type in the template; (b) detecting the signal from the mixed population, wherein the fraction of the first nucleotide type compared to the second nucleotide type is increased in the mixed population over at least two of the cycles of the nucleic acid sequencing process. Optionally, the polymerase is removed from the mixed population prior to (b).

An example of a nucleic acid sequencing process that can be modified to use a fractionally labeled mixture of nucleotides is sequencing-by-synthesis (SBS). SBS generally involves the enzymatic extension of a nascent primer through the iterative addition of nucleotides against a template strand to which the primer is hybridized. Briefly, SBS can be initiated by contacting target nucleic acids, attached to sites in a flow cell, with one or more labeled nucleotides, DNA polymerase, etc. The nucleotides used for the primer extension step can be from a fractionally labeled mixture of nucleotides. Those sites where a primer is extended using the target nucleic acid as template will incorporate either a labeled nucleotide that can be detected or a non-labeled nucleotide. In the case where an ensemble of nucleic acids is used, the ensemble will be fractionally labeled following the primer extension step. Detection can use an apparatus or method set forth herein. Optionally, a nucleotide that is incorporated into the primer, whether labeled species or not, can further include a reversible terminator moiety that terminates further primer extension once the nucleotide has been added to a primer. For example, a nucleotide having a reversible terminator moiety can be added to a primer such that subsequent extension cannot occur until a deblocking agent is delivered to remove the moiety. Thus, for embodiments that use reversible termination, a deblocking reagent can be delivered to the vessel (before or after detection occurs).

Washes can be carried out between the various delivery steps in an SBS method. The cycles can be performed n times to extend the primer by n nucleotides, thereby detecting a sequence of length n. Exemplary SBS procedures, reagents and detection components that can be readily adapted for use with a fractionally labeled mixture of nucleotides are described, for example, in Bentley et al., *Nature* 456:53-59 (2008), WO 04/018497; WO 91/06678; WO 07/123744; U.S. Pat. Nos. 7,057,026; 7,329,492; 7,211,414; 7,315,019 or 7,405,281, or US Pat. App. Pub. No. 2008/0108082 A1, each of which is incorporated herein by reference. Other SBS methods that can be similarly modified are those that are commercially available from Illumina, Inc. (San Diego, Calif.). Exemplary SBS methods from Illumina, Inc. include those that are marketed for use on the HiSeq™, MiSeq™, NextSeq™, or NovaSeq™ platforms.

Sequencing-by-ligation reactions can also be modified to use fractional labeling methods, compositions or apparatus. For example, ligation probes can be fractionally labeled and used in place of labeled probes in methods such as those set forth in Shendure et al. *Science* 309:1728-1732 (2005); U.S. Pat. No. 5,599,675; or U.S. Pat. No. 5,750,341, each of which is incorporated herein by reference. Sequencing-by-hybridization (SBH) procedures can also be modified to employ fractionally labeled mixtures of probes. Exemplary SBH methods are described in Bains et al., *Journal of Theoretical Biology* 135 (3), 303-7 (1988); Drmanac et al., *Nature Biotechnology* 16, 54-58 (1998); Fodor et al., *Science* 251 (4995), 767-773 (1995); or WO 1989/10977, each of which is incorporated herein by reference. In both sequencing-by-ligation and sequencing-by-hybridization procedures, primers that are hybridized to nucleic acid templates are subjected to repeated cycles of extension by oligonucleotide ligation. Typically, the oligonucleotides are fluorescently labeled and can be detected to determine the sequence of the template, for example, using fractional labeling compositions and methods set forth herein.

Throughout this application various publications, patents and/or patent applications have been referenced. The disclosures of these documents in their entireties are hereby incorporated by reference in this application.

A number of embodiments have been described. Nevertheless, it will be understood that various modifications may be made. Accordingly, other embodiments are within the scope of the following claims.

What is claimed is:

1. A method for sequencing a population of nucleic acids, comprising
    subjecting a population of primer-template nucleic acid hybrids to multiple cycles of a nucleic acid sequencing process, wherein the templates share a common sequence, wherein each of the cycles comprises:
    (a) forming a mixed population comprising primer-template nucleic acid hybrids that are bound to a first nucleotide type and primer-template nucleic acid hybrids that are bound to a second nucleotide type, wherein the first nucleotide type comprises an exogenous label that produces a first signal and wherein the second nucleotide type is substantially devoid of labels that produce the first signal, wherein the first and second nucleotide types are cognates for the same base type in the template, and
    (b) detecting the signal from the mixed population, wherein the fraction of the first nucleotide type is increased in the mixed population over at least two of the cycles of the nucleic acid sequencing process.

2. The method of claim 1, wherein the nucleotides are noncovalently bound to the primer-template nucleic acid hybrids via stabilized ternary complexes in step (a).

3. The method of claim 2, wherein the stabilized ternary complexes are present in the mixed population during step (b).

4. The method of claim 3, wherein each of the cycles further comprises (c) adding a reversibly terminated nucleotide to each of the primers of the primer-template nucleic acid hybrids, thereby producing reversibly terminated primers.

5. The method of claim 4, wherein each of the cycles further comprises deblocking the reversibly terminated primers.

6. The method of claim 4, wherein the reversibly terminated nucleotide that is added to each of the primers is substantially devoid of exogenous labels.

7. The method of claim 4, wherein each of the cycles further comprises dissociating the ternary complexes prior to the adding of the reversibly terminated nucleotide to each of the primers.

8. The method of claim 1, wherein the nucleotides are covalently bound to the primers via polymerase catalyzed primer extension in step (a).

9. The method of claim 8, wherein the nucleotides that are covalently bound to the primer-template nucleic acid hybrids each comprise a reversible terminator moiety, thereby producing reversibly terminated primers.

10. The method of claim 9, wherein each of the cycles further comprises deblocking the reversibly terminated primers.

11. The method of claim 1, wherein the fraction of the first nucleotide type is cumulatively increased in the mixed population over at least three of the cycles of the nucleic acid sequencing process.

12. The method of claim 1, wherein the cycles are repeated at least 10 times to acquire a sequence that is at least 10 nucleotides long.

13. The method of claim 12, wherein the primers of the primer-template nucleic acid hybrids are extended to a subsequent position in the common sequence of the templates during each of the cycles.

14. The method of claim 1, wherein the population of primer-template nucleic acid hybrids is attached to a site in an array of primer-template nucleic acid hybrid sites.

15. The method of claim 1, wherein the population of primer-template nucleic acid hybrids comprises amplicons of the template.

16. The method of claim 1, wherein the mixed population is illuminated by a laser in step (b).

17. The method of claim 1, wherein the fraction of the first nucleotide type in the mixed population is increased by at least 10% over the course of the nucleic acid sequencing process.

18. The method of claim 1, wherein the exogenous label comprises a fluorescent label that is excited at a first wavelength and wherein the second nucleotide type is substantially devoid of fluorescent labels that are excited at the first wavelength.

19. The method of claim 18, wherein step (b) comprises illuminating the mixed population at the first wavelength and detecting fluorescent emission from the fluorescent label.

20. A method for sequencing a population of nucleic acids, wherein the nucleic acids comprise templates sharing a common sequence, comprising:
    (a) binding the population of nucleic acids with a first fractionally labeled mixture of nucleotides, thereby forming a first fractionally labeled population of nucleic acids,
    wherein the first mixture comprises nucleotide cognates for a common base type in the templates, and
    wherein a fraction of the nucleotide cognates for the common base type in the mixture are exogenously labeled nucleotides that produce a signal that is not produced by other nucleotide cognates for the common base type in the mixture;
    (b) detecting the signal from the first fractionally labeled population of nucleic acids; and
    (c) repeating steps (a) and (b) using a second mixture of fractionally labeled nucleotides, wherein the fraction of exogenously labeled nucleotides is higher in the second mixture compared to the first mixture.

* * * * *